(12) United States Patent
Nagy et al.

(10) Patent No.: US 9,701,771 B2
(45) Date of Patent: Jul. 11, 2017

(54) SUBSTITUTED ZIRCONOCENES CATALYSTS AND METHODS OF USE IN POLYMERIZATION REACTIONS

(71) Applicant: Basell Polyolefine GmbH, Wesseling (DE)

(72) Inventors: Sandor Nagy, Webster, TX (US); Shahram Mihan, Bad Soden (DE); Linda N. Winslow, Cincinnati, OH (US); Ilya E. Nifant'ev, Moscow (RU); Pavel V. Ivchenko, Moscow (RU); Vladimir V. Bagrov, Moscow (RU); Igor A. Kashulin, Moscow (RU)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 14/677,690

(22) Filed: Apr. 2, 2015

(65) Prior Publication Data

US 2015/0284490 A1    Oct. 8, 2015

Related U.S. Application Data

(60) Provisional application No. 61/974,853, filed on Apr. 3, 2014.

(51) Int. Cl.
*C07F 17/00* (2006.01)
*C08F 4/6592* (2006.01)
*C08F 10/00* (2006.01)
*C08F 210/16* (2006.01)
*C08F 4/659* (2006.01)

(52) U.S. Cl.
CPC ............ *C08F 210/16* (2013.01); *C07F 17/00* (2013.01); *C08F 4/65925* (2013.01); *C08F 4/65912* (2013.01)

(58) Field of Classification Search
CPC ...... C07F 17/00; C08F 4/65925; C08F 10/00; C08F 210/02
See application file for complete search history.

(56) References Cited

U.S. PATENT DOCUMENTS

| | | | | |
|---|---|---|---|---|
| 6,160,064 A | * | 12/2000 | Waymouth | .............. C08F 10/00 526/134 |
| 2001/0049425 A1 | * | 12/2001 | Waymouth | .............. C08F 10/00 526/126 |

* cited by examiner

*Primary Examiner* — Caixia Lu

(57) ABSTRACT

The present disclosure relates to metallocene catalysts for use in polymerization processes. Such catalysis may be used to generate long chain polymers with low long chain branching and high molecular weights. Additionally, the size of the polymers produced can be controlled by modifying the ratio of MAO or other activator to metallocene catalyst.

4 Claims, No Drawings

SUBSTITUTED ZIRCONOCENES CATALYSTS AND METHODS OF USE IN POLYMERIZATION REACTIONS

CROSS-REFERENCE TO RELATED APPLICATIONS

This application claims benefit of priority under 35 U.S.C. §119(e) of U.S. Provisional Application No. 61/974,853 filed Apr. 3, 2014, the contents of which are incorporated herein by reference in their entirety.

BACKGROUND

I. Technical Field

In general, the present disclosure relates to polymerization catalysts and methods of using such catalysts in the production of polyethylene.

II. Background

Metallocenes are considered attractive catalyst components for applications in the production of polymers. In particular, non-bridged zirconocenes have been identified as attractive low cost catalysts for use in polymerization processes where little to no long-chain branching is desired. When looking at the performance of these catalysts, the development of catalysts typically focuses on maximizing both the activity and the maximum potential molecular weight of the resultant polymer. Ansa-bridged metallocenes tend to increase the amount of long-chain branching in the resultant polymer. Finally, hafnocenes can also be used to generate polymers but the catalysts are significantly more expensive and the catalytic activity is low compared to the zirconocenes based catalysts. Thus, a need still exists to develop highly active catalysts which can generate high molecular weight polymers with minimal long-chain branching.

Furthermore, many of the metallocene catalysts require a high ratio of aluminum from MAO to the metallocene catalysts in order to activate the catalyst. In these catalytic systems, the ratio of MAO to catalyst can reach over 100 to 1 thus greatly increasing the cost of using the catalysts. Other catalytic activators, such as perfluorophenyl borates, are expensive to use compared to MAO. Given that the activator is required in order for polymerization to occur, the activator provides another area of control to fine tune the product of the polymerization. The development of polymerization catalyst which becomes active at a relatively low amount of MAO or other activator would decrease the cost of producing the polymers. Furthermore, the development of a polymerization catalyst which allows the polymer produced to vary based upon the amount of activator used could allow for a simpler mechanism to control the properties of the polymer produced. Such a development would improve the ability to control the synthesis at a more detailed level through a simple mechanism reducing the complexity of production.

SUMMARY

In general, the present disclosure provides metallocene complexes for use as alkene polymerization catalysts.

In some aspects, the present disclosure provides a compound of the formula:

(I)

wherein: $L_1$ and $L_2$ are each independently a ligand of the formula:

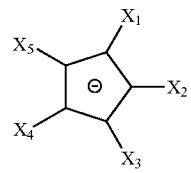
(II)

wherein: $X_1$ is alkyl$_{C\leq 6}$, alkenyl$_{C\leq 6}$, or a substituted version of either of these groups; and $X_2$, $X_3$, and $X_4$ are each independently hydrogen, alkyl$_{C\leq 8}$, alkenyl $_{C\leq 8}$, alkynyl $_{C\leq 8}$, aryl $_{C\leq 12}$, aralkyl $_{C\leq 12}$, heterocycloalkyl $_{C\leq 12}$, heteroaryl $_{C\leq 12}$, or a substituted version of any of these groups; $X_5$ is hydrogen, alkyl$_{C\leq 8}$ or a substituted alkyl$_{C\leq 8}$; M is a transition metal of Group 4; and $Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, aralkyloxylate, or a substituted version of any of these groups; with the proviso that if $X_1$ is alkyl$_{C\leq 3}$, then $X_2$, $X_3$, and $X_4$ are not all hydrogen or alkyl$_{C\leq 8}$. In some embodiments, $L_1$ and $L_2$ are each independently a ligand of the formula:

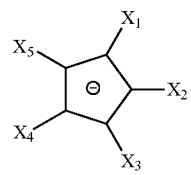
(II)

wherein: $X_1$ is alkyl$_{C\leq 6}$, alkenyl$_{C\leq 6}$, or a substituted version of either of these groups; and $X_2$, $X_3$, and $X_4$ are each independently hydrogen, alkyl$_{C\leq 8}$, alkenyl $_{C\leq 8}$, alkynyl $_{C\leq 8}$, aryl $_{C\leq 12}$, aralkyl $_{C\leq 12}$, heterocycloalkyl $_{C\leq 12}$, heteroaryl $_{C\leq 12}$, or a substituted version of any of these groups; $X_5$ is hydrogen, alkyl$_{C\leq 8}$ or a substituted alkyl$_{C\leq 8}$; with the proviso that if $X_1$ is alkyl$_{C\leq 3}$, then $X_2$, $X_3$, and $X_4$ are not all hydrogen or alkyl$_{C\leq 8}$. In some embodiments, $X_1$ is alkyl$_{C\leq 6}$. In some embodiments, $X_1$ is methyl, butyl, cyclopentyl, or cyclohexyl. In some embodiments, $X_2$ is hydrogen. In other embodiments, $X_2$ is alkyl$_{C\leq 6}$. In some embodiments, $X_2$ is methyl or butyl. In some embodiments, $X_3$ is hydrogen. In other embodiments, $X_3$ is alkyl$_{C\leq 6}$. In some embodiments, $X_3$ is methyl, cyclopentyl, or cyclohexyl. In some embodiments, $X_3$ is substituted aryl$_{C\leq 12}$. In some embodiments, the aryl$_{C\leq 12}$ further comprises a haloalkane$_{C\leq 4}$. In some embodiments, the haloalkane$_{C\leq 4}$ is a trifluoromethyl group. In some embodiments, $X_3$ is 4-trifluoromethylphenyl or 3-trifluoromethylphenyl. In other embodiments, $X_3$ is heteroaryl$_{C\leq 12}$. In some embodiments, $X_3$ is 2-methyl-furanyl or 2-methylthiophenyl. In some embodiments, $X_4$ is hydrogen. In other embodiments, $X_4$ is substituted aryl$_{C≤12}$. In some embodiments, the aryl$_{C≤12}$ further comprises a haloalkane$_{C≤4}$. In some embodiments, the haloalkane$_{C≤4}$ is a trifluoromethyl group. In some embodiments, $X_4$ is 4-trifluoromethylphenyl, 3-trifluoromethylphenyl, or 3,5-di(trifluoromethyl)phenyl. In other embodiments, $X_4$ is heteroaryl$_{C≤12}$. In some embodiments, $X_4$ is 2-methylfuranyl. In some embodiments, $X_3$ or $X_4$ are substituted aryl$_{(C≤18)}$. In some embodiments, the substituted aryl$_{(C≤18)}$ further comprises one, two, three, or four haloalkane$_{(C≤3)}$ groups. In some embodiments, the haloalkane$_{(C≤3)}$ is a trifluoromethyl group. In some embodiments, $X_5$ is hydrogen. In some embodiments, $L_1$ and $L_2$ are each independently selected from:

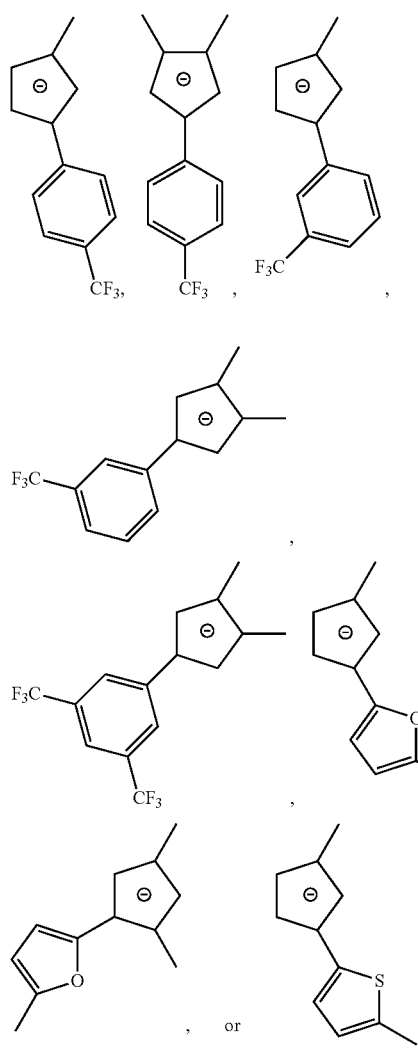

In some embodiments, M is Ti, Zr, or Hf. In some embodiments, M is Zr. In some embodiments, $Y_1$ and $Y_2$ are each independently halide. In some embodiments, $Y_1$ and $Y_2$ are each independently chloride. In some embodiments, the formula is further defined as:

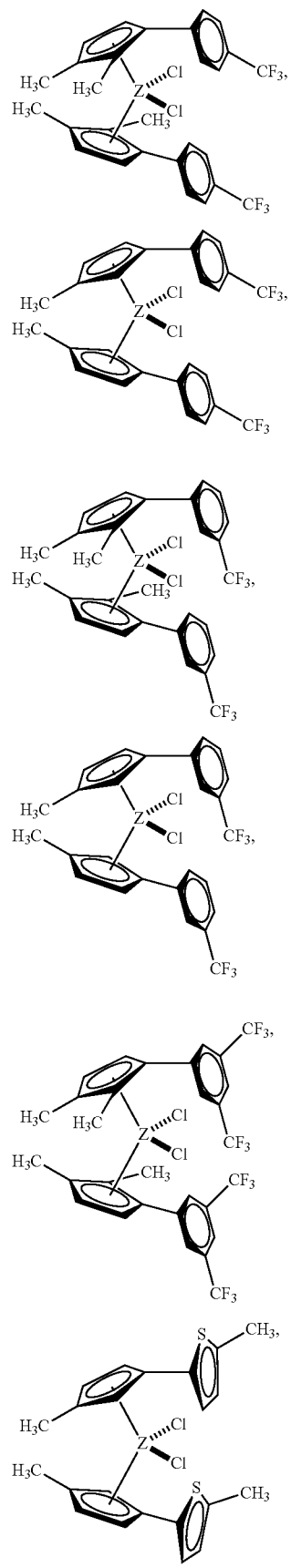

-continued

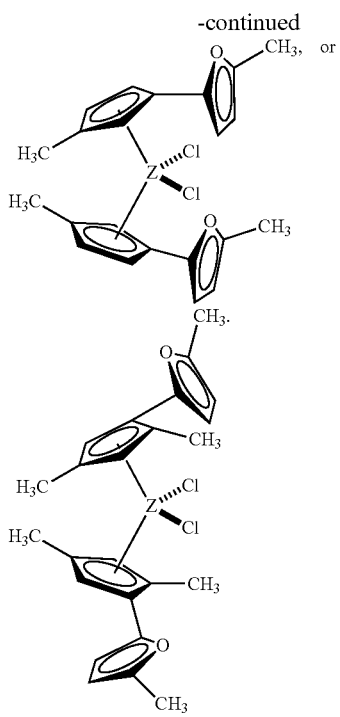

In another aspect, the present disclosure provides a method comprises reacting a terminal alkene monomer with any catalyst composition disclosed herein to generate a long chain polymer. In some embodiments, the polymer contains a long chain backbone with less than 10% long chain branching. In other embodiments, the polymer contains a long chain backbone with less than 5% long chain branching. In other embodiments, the polymer contains a long chain backbone with less than 1% long chain branching. In some embodiments, the terminal alkene is reacted using a gas, slurry, or solution polymerization process. In some embodiments, the terminal alkene is reacted using a hybrid catalyst polymerization technique. In some embodiments, the terminal alkene is ethylene.

In yet another aspect, the present disclosure provides a method of making a long straight chain polyethylene polymer, wherein the method comprises reacting the monomer, ethylene, with a catalyst of the present disclosure. In some embodiments, the polymer contains a long chain backbone with less than 10% long chain branching. In other embodiments, the polymer contains a long chain backbone with less than 5% long chain branching. In other embodiments, the polymer contains a long chain backbone with less than 1% long chain branching. In some embodiments, the ethylene is reacted using a gas, slurry, or solution polymerization process. In some embodiments, the ethylene is reacted using a slurry polymerization process. In some embodiments, the slurry polymerization process is an isobutane slurry process reacted in an autoclave. In some embodiments, the ethylene is reacted using a hybrid catalyst polymerization technique. In some embodiments, the reaction is run at a temperature from about 50° C. to about 100° C. In some embodiments, the reaction is run at a temperature of about 70° C. In some embodiments, the reaction is run with a pressure of ethylene from about 1 bar to about 30 bar of ethylene. In some embodiments, the reaction is run with a pressure of ethylene of about 15 bar. In some embodiments, the reaction contains an optionally co-monomer. In some embodiments, the co-monomer is a terminal alkene$_{C\leq 18}$ or terminal aralkene$_{C\leq 18}$. In some embodiments, the co-monomer is 1-butene, 1-pentene, 1-hexene, 1-octene, or 1-decene. In some embodiments, the co-monomer is 1-butene, 1-hexene, or 1-octene. In some embodiments, the co-monomer is 1-butene. In some embodiments, the co-monomer is 1-hexene. In some embodiments, the co-monomer is 1-octene. In some embodiments, the co-monomer is present in a ratio from about 1:2 to about 1:20 butene to diluent. In some embodiments, the co-monomer is present in a ratio of about 1:10 with a diluent. In some embodiments, the diluent is an aliphatic solvent, aromatic solvent, or a halogenated version of either solvent. In some embodiments, the diluent is butane, pentane, hexane, heptane, cyclohexane, benzene, toluene, xylene, dichloromethane, chloroform, chlorobenzene, or dichloroethane. In some embodiments, the diluent is isobutane or hexane. In some embodiments, the diluent is isobutane. In some embodiments, the diluent is hexane. In some embodiments, the reaction is run with aluminoxane cocatalyst. In some embodiments, aluminoxane is further defined by the formulas:

(Al(R)O)$_x$     (III)

or

R-(Al(R)O)$_y$—AlR$_2$     (IV)

wherein: R is alkyl$_{C\leq 6}$; x is 3-50; and y is 1-50. In some embodiments, R is methyl. In some embodiments, y is from about 10 to about 20. In some embodiments, x is from about 3 to about 20. In some embodiments, the aluminoxane is methyl aluminoxane (MAO). In some embodiments, the MAO is on a solid support. In some embodiments, the solid support is silica. In some embodiments, the amount of MAO added to the reaction changes the molecular weight of the polymer produced. In some embodiments, increasing the amount of MAO in the reaction reduces the molecular weight of the resultant polymer. In some embodiments, the reaction also optionally contains H$_2$ gas. In some embodiments, the reaction is run at a H$_2$ pressure of 20 dpsi/300 mL. In some embodiments, the reaction is run for between 0.1 to 6 hours. In some embodiments, the reaction is run for between 0.5 to 2.5 hours. In some embodiments, the reaction is run for 1 hour. In some embodiments, the molecular weight of the polyethylene polymer is greater than 300,000 daltons. In some embodiments, the activity of the catalyst shows an activity of greater than 800 g/g/h.

In another aspect, the present disclosure provides a method of producing a polyolefin polymer comprising a) admixing to a reaction mixture a terminal alkene$_{(C\leq 12)}$ to a pressure from about 1 bar to about 30 bars, a diluent, a metallocene catalyst of claims 1-4, and an activating compound defined by the formula:

(Al(R)O)$_x$     (III)

or

R-(Al(R)O)$_y$—AlR$_2$     (IV)

wherein: R is alkyl$_{(C\leq 6)}$; x is 3-50; and y is 1-50; or

B(X$_1$)(X$_2$)(X$_3$)     (V)

wherein: X$_1$, X$_2$, and X$_3$ are each independently hydroxy, alkyl$_{(C\leq 12)}$, aryl$_{(C\leq 12)}$, haloalkyl$_{(C\leq 12)}$, or haloaryl$_{(C\leq 12)}$; b) heating the reaction mixture to a temperature from about 30° C. to about 100° C.; and c) contacting the terminal alkene$_{(C\leq 12)}$ with the metallocene catalyst under conditions sufficient to produce a polyolefin polymer. In some embodiments, the terminal alkene$_{(C\leq 12)}$ is ethylene. In some embodiments, the polyolefin polymer is polyethylene. In some embodiments, the terminal alkene$_{(C\leq 12)}$, the diluent, the metallocene catalyst, or the activating compound are added in any order. In some embodiments, the terminal alkene$_{(C\leq 12)}$ is added first. In some embodiments, the diluent is added next. In some embodiments, the metallocene catalyst and the activating compound are added together. In other embodiments, the activating compound is added and then the metallocene catalyst. In other embodiments, the metallocene catalyst is added and then the activating compound is added. In some embodiments, the reaction mixture optionally comprises a 1-butene, 1-hexene, or 1-octene co-monomer. In some embodiments, the characteristics of the polyolefin polymer are controlled by the ratio of the catalyst to the activator. In some embodiments, the diluent is isobutene. In some embodiments, the aluminoxane is methyl aluminoxane (MAO). In some embodiments, the reaction mixture also optionally comprises H$_2$ gas.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

DESCRIPTION OF ILLUSTRATIVE EMBODIMENTS

I. Polymerization Catalysts

In some aspects, the present disclosure provides novel polymerization catalysts for the preparation of long chain olefin polymers with little to no branching points. In some embodiments, the polymerization catalyst is a metallocene derivative with trifluoromethylaryl-substituted cyclopentadienyl ligands or with heteroaryl-substituted cyclopentadienyl ligands. In some embodiments, the catalysts comprise Group 4 metal atoms, for example, zirconium or hafnium.

Table 1 identifies catalysts and catalyst precursors discussed herein, including the novel compounds provided, as well as comparison compounds that are compared herein. The compounds listed in Table 1 correspond to the following formula:

TABLE 1

| Run # | M | L$_1$ | L$_2$ |
|---|---|---|---|
| \multicolumn{4}{c}{"Benchmarks"} |
| 1 | Zr | 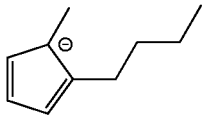 | 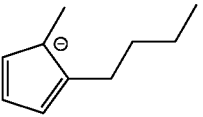 |
| 2 | Zr | 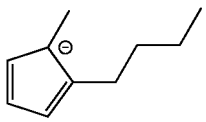 | 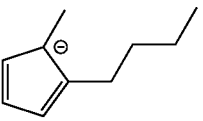 |
| 3 | Hf | 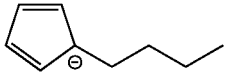 | 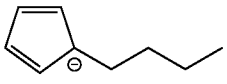 |
| 4 | Hf | 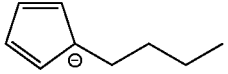 | 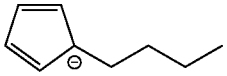 |
| 5 | Hf | 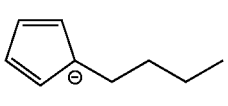 | 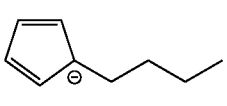 |
| \multicolumn{4}{c}{(R-Alk-Cp)$_2$} |
| 6 | Zr | 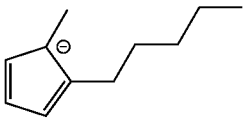 | 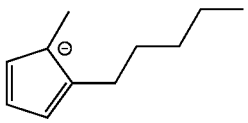 |

TABLE 1-continued
Metallocene Polymerization Catalysts
| Run # | M | L$_1$ | L$_2$ |
|---|---|---|---|
| 7 | Zr | 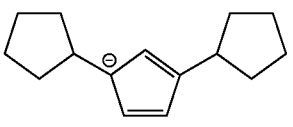 | 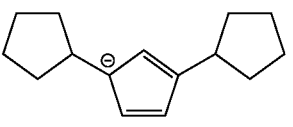 |
| 8 | Zr | 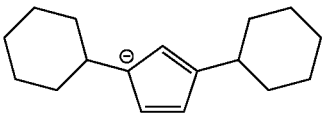 | 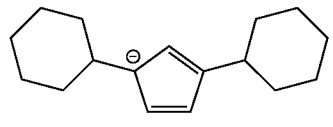 |
| 9 | Zr | 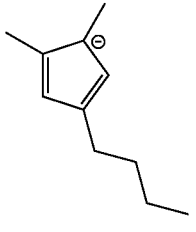 | 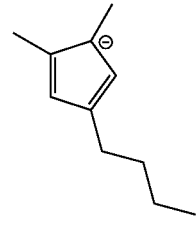 |
| 10 | Zr | 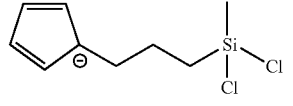 | 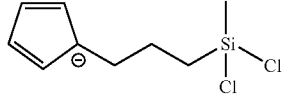 |
| 11 | Zr | 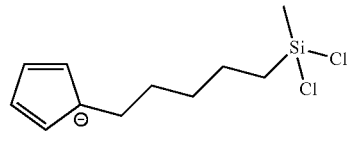 | 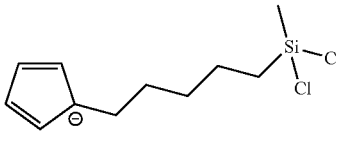 |
| 12 | Zr | 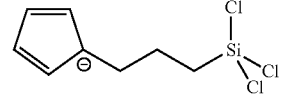 | 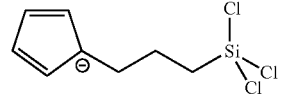 |
| 13 | Zr | 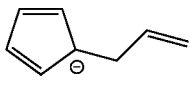 | 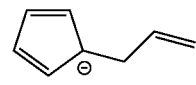 |
| 14 | Zr | 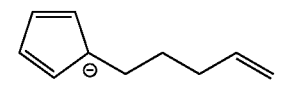 | 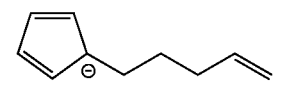 |
| 15 | Zr | 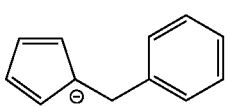 | 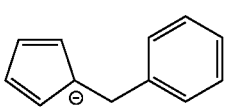 |
| 16 | Zr | 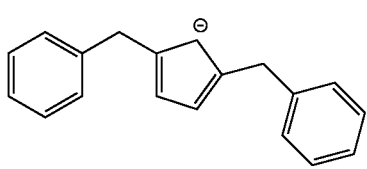 | 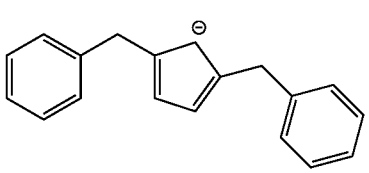 |
| 17 | Hf | 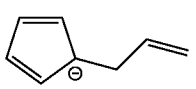 | 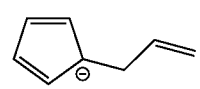 |
| 18 | Hf | 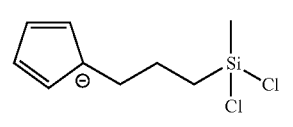 | 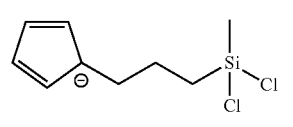 |

TABLE 1-continued

Metallocene Polymerization Catalysts

| Run # | M | L₁ | L₂ |
|---|---|---|---|
| | | (R)-Alk-Cp)(Ind) | |
| 19 | Zr | cyclopentadienyl anion | indenyl anion |
| 20 | Zr | cyclopentadienyl anion | methyl-substituted dibenzofluorenyl anion |
| 21 | Zr | cyclopentadienyl anion | indenyl anion with propyl-Si(Me)Cl₂ substituent |
| 22 | Zr | n-butyl-substituted cyclopentadienyl anion | methyl-substituted dibenzofluorenyl anion |
| 23 | Zr | allyl-substituted cyclopentadienyl anion | indenyl anion |
| 24 | Zr | cyclopentadienyl anion with propyl-Si(Me)Cl₂ substituent | indenyl anion |
| 25 | Zr | n-butyl-substituted cyclopentadienyl anion | 2,2-dimethyl-cyclopenta-fluorenyl anion |
| 26 | Zr | cyclopentadienyl anion | hexahydro-substituted fluorenyl anion |

TABLE 1-continued
Metallocene Polymerization Catalysts
| Run # | M | L₁ | L₂ |
|---|---|---|---|
| | | (Ind)₂ | |
| 27 | Zr | 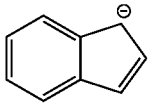 | 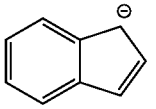 |
| 28 | Zr | 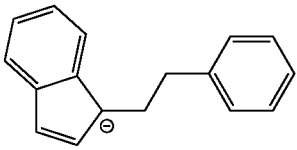 | 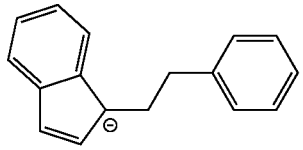 |
| 29 | Zr | 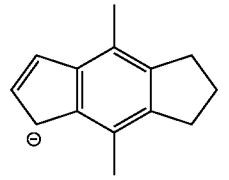 | 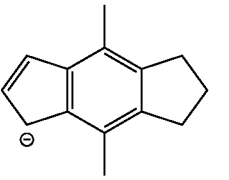 |
| 30 | Zr | 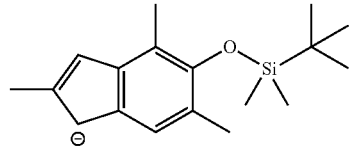 | 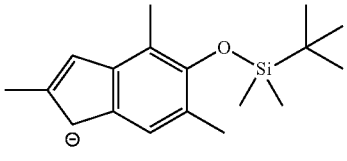 |
| 31 | Zr | 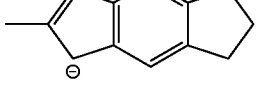 | 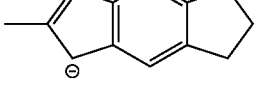 |
| 32 | Zr | 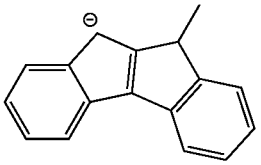 | 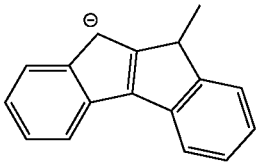 |
| 33 | Zr | 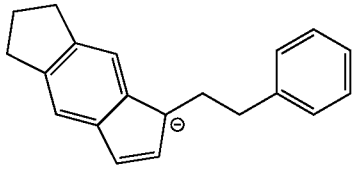 | 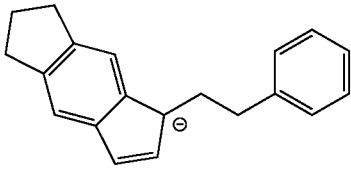 |
| 34 | Zr | 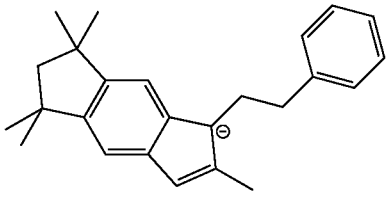 | 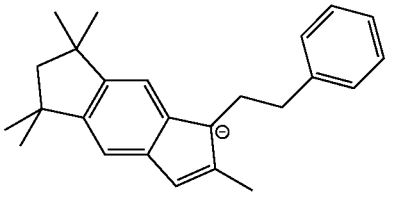 |
| 35 | Zr | 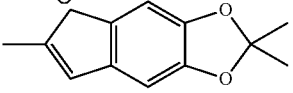 | 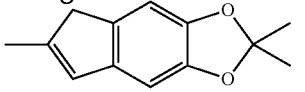 |

TABLE 1-continued

Metallocene Polymerization Catalysts

| Run # | M | L₁ | L₂ |
|---|---|---|---|
| 36 | Zr | 2-methyl-2,2-dimethyl-s-indacenyl anion | 2-methyl-2,2-dimethyl-s-indacenyl anion |
| 37 | Zr | indenyl anion | 4,6-dimethyl-5-(tert-butyldimethylsilyloxy)indenyl anion |
| 38 | Zr | indenyl anion | 2,4,6-trimethyl-5-(hex-5-enyldimethylsilyloxy)indenyl anion |

(Ar-Cp)₂

| 39 | Zr | 2,5-diphenylcyclopentadienyl anion | 2,5-diphenylcyclopentadienyl anion |
| 40 | Zr | 2-phenyl-5-(2-naphthyl)cyclopentadienyl anion | 2-phenyl-5-(2-naphthyl)cyclopentadienyl anion |
| 41 | Zr | 2-methyl-5-phenylcyclopentadienyl anion | 2-methyl-5-phenylcyclopentadienyl anion |
| 42 | Zr | 2-(5-methylthien-2-yl)-5-phenylcyclopentadienyl anion | 2-(5-methylthien-2-yl)-5-phenylcyclopentadienyl anion |
| 43 | Zr | 2-methyl-4-(4-methylphenyl)cyclopentadienyl anion | 2-methyl-4-(4-methylphenyl)cyclopentadienyl anion |
| 44 | Zr | 2-methyl-4-(4-chlorophenyl)cyclopentadienyl anion | 2-methyl-4-(4-chlorophenyl)cyclopentadienyl anion |
| 45 | Zr | 2-methyl-4-(4-tert-butylphenyl)cyclopentadienyl anion | 2-methyl-4-(4-tert-butylphenyl)cyclopentadienyl anion |
| 46 | Zr | 2,3-dimethyl-5-phenylcyclopentadienyl anion | 2,3-dimethyl-5-phenylcyclopentadienyl anion |

TABLE 1-continued
Metallocene Polymerization Catalysts
| Run # | M | L₁ | L₂ |
|---|---|---|---|
| 47 | Zr | 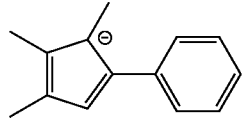 | 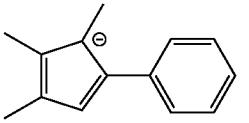 |
| 48 | Zr | 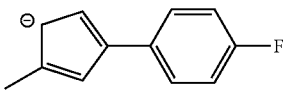 | 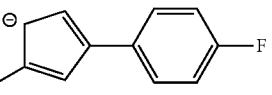 |
| 49 | Zr | 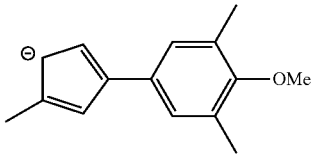 | 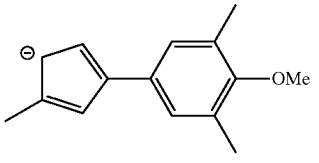 |
| 50 | Zr | 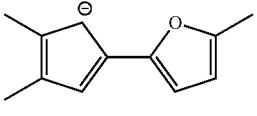 | 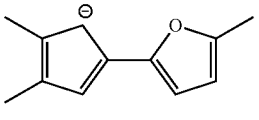 |
| 51 | Zr | 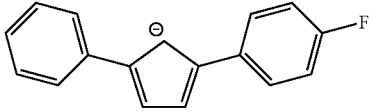 | 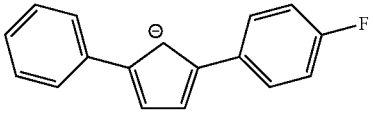 |
| 52 | Zr | 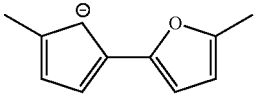 | 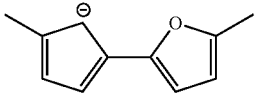 |
| 53 | Zr | 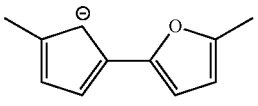 | 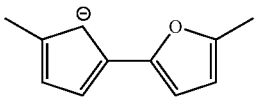 |
| 54 | Zr | 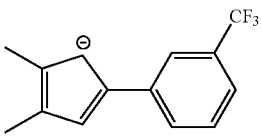 | 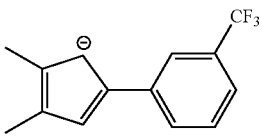 |
| 55 | Zr | 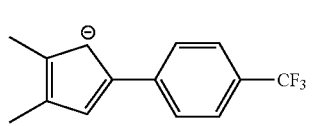 | 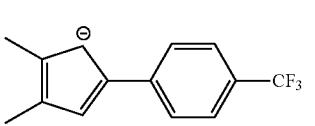 |
| 56 | Zr | 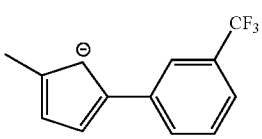 | 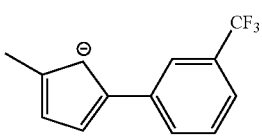 |
| 57 | Zr | 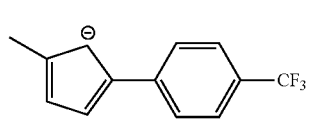 | 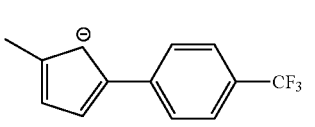 |

TABLE 1-continued

Metallocene Polymerization Catalysts

| Run # | M | L₁ | L₂ |
|---|---|---|---|
| 58 | Zr | 2,3-dimethyl-5-(3-fluorophenyl)cyclopentadienyl | 2,3-dimethyl-5-(3-fluorophenyl)cyclopentadienyl |
| 59 | Zr | 2,3-dimethyl-5-(3,5-bis(trifluoromethyl)phenyl)cyclopentadienyl | 2,3-dimethyl-5-(3,5-bis(trifluoromethyl)phenyl)cyclopentadienyl |
| 60 | Zr | 2-methyl-5-(5-methylthiophen-2-yl)cyclopentadienyl | 2-methyl-5-(5-methylthiophen-2-yl)cyclopentadienyl |
| 61 | Zr | 2-methyl-5-(3-fluorophenyl)cyclopentadienyl | 2-methyl-5-(3-fluorophenyl)cyclopentadienyl |
| 62 | Zr | (pentafluorophenyl)cyclopentadienyl | (pentafluorophenyl)cyclopentadienyl |

(R-Alk-Cp)(Ar-Cp)

| Run # | M | L₁ | L₂ |
|---|---|---|---|
| 63 | Zr | n-butylcyclopentadienyl | 1,2,4-triphenylcyclopentadienyl |
| 64 | Zr | allylcyclopentadienyl | 2,3-dimethyl-5-phenylcyclopentadienyl |
| 65 | Zr | n-butylcyclopentadienyl | 2-methyl-5-phenylcyclopentadienyl |
| 66 | Zr | 3-(dichloro(methyl)silyl)propylcyclopentadienyl | 2,3-dimethyl-5-phenylcyclopentadienyl |

TABLE 1-continued

Metallocene Polymerization Catalysts

| Run # | M | L₁ | L₂ |
|---|---|---|---|

(Ind)(Ar-Cp)

| 67 | Zr | indenyl anion | 2,3-dimethyl-5-phenyl-cyclopentadienyl anion |
| 68 | Zr | indenyl anion | 2,5-diphenyl-cyclopentadienyl anion |
| 69 | Zr | indenyl anion | tetraphenyl-cyclopentadienyl anion |
| 70 | Zr | indenyl anion | 5-(5-methylthien-2-yl)-3-phenyl-cyclopentadienyl anion |

The compounds provided by the present disclosure are shown above in the summary section and in the claims below. In some embodiments, these compounds are made using the methods outlined in the Examples section. In some embodiments, the compounds of the present disclosure may be synthesized using a method such as that described in Scheme 1. In some embodiments, using an unsubstituted or substituted aryl halide, the aryl halide is reacted with BuLi in a nonpolar solvent such as THF using a 2 to 1 ratio of BuLi to halide. In some embodiments, the resultant product is then reacted with an equivalent of the desired cyclopentadiene. Then, in some embodiments, the reaction is worked up using a proton source such as p-toluenesulfonic acid and then is extracted to yield the desired cyclopentadiene ligand derivative. In some embodiments, the resultant cylcopentadiene ligand is reacted with an equivalent of BuLi in an ether solvent. In some embodiments, after the reaction with BuLi, a half equivalent of ZrCl₄(THF)₂ is added to the reaction mixture. In some embodiments, the complex precipitates out of solution and is purified through extraction to obtain the desired metallocene complex.

Scheme 1: Generalized synthetic scheme for the preparation of bisaryl metallocenes

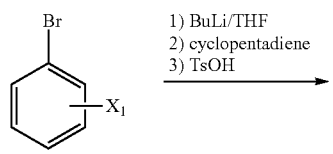

1) BuLi/THF
2) cyclopentadiene
3) TsOH

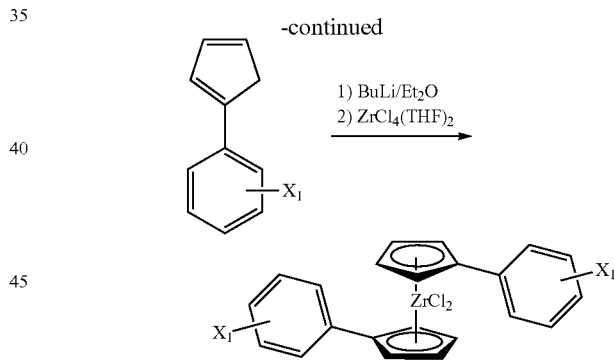

These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

In some embodiments, the organometallic complexes provided herein is used to generate a catalytically active species which reacts with an alkene monomer to catalyze the production of a polymer. In some embodiments, the π electrons of the alkene form a bond to the metal center which activates the alkene for the next step in the reaction. In some embodiments, the alkene may also undergo oxidative addition to the metal center during the polymerization mechanism. Such catalytic mechanisms are be well known in the art and are taught by *Handbook of Polymer Synthesis Part A* by Kricheldorf, et al., *Principles of Polymerization* by Odian, and *Advanced Inorganic Chemistry, 5ᵗʰ Edition* by Cotton and Wilkinson, for example. In alkene polymerization, in some embodiments, for example, the organometallic catalyst is a metallocene which contains a metal of Group 4.

In some embodiments, while a complex is a particular metal in the examples, complexes using other metals within the same group on the periodic table so long as those elements are stable are also contemplated. It is contemplated that a metallocene with a zirconium metal core may in other catalysts contain a hafnium or a titanium metal core. Additionally, in some embodiments, the labile nature of the ligands around the metallocene affects the reactivity of the catalyst or competes with the alkene's ability to bind to the metal center.

In some embodiments, compounds of the disclosure also have the advantage that they is more catalytically active than, offer more precise control of the resulting polymer, requires a smaller amount of an activating agent, such as aluminoxane, in order to become catalytically active, and/or have other useful physical or chemical properties over compounds known in the prior art, whether for use in the processes stated herein or otherwise. In some embodiments, the size of the polymer is controlled by adjusting the ratio of MAO to the metal catalysts. In some embodiments, the higher ratios of MAO to metal lead to less active catalysts and decreased molecular weight of the resultant polymer.

In some embodiments, compounds employed in methods of the disclosure contains one or more asymmetrically-substituted carbon or nitrogen atoms, and is isolated in optically active or racemic form. Thus, all chiral, diastereomeric, racemic form, epimeric form, and all geometric isomeric forms of a structure are intended, unless the specific stereochemistry or isomeric form is specifically indicated. In some embodiments, compounds occur as racemates and racemic mixtures, single enantiomers, diasteromeric mixtures and individual diastereomers. In some embodiments, a single diastereomer is obtained. The chiral centers of the compounds of the present disclosure can have the S or the R configuration, as defined by the IUPAC 1974 Recommendations. For example, mixtures of stereoisomers may be separated using the techniques taught in the examples and the general chemical literature including, for example, *Advanced Inorganic Chemistry, 5th Edition* by Cotton and Wilkinson and *March's Advanced Organic Chemistry: Reactions, Mechanisms, and Structure* (2007), as well as modifications thereof.

Atoms making up the compounds of the present disclosure are intended to include all isotopic forms of such atoms. Compounds of the present disclosure include those with one or more atoms that have been isotopically modified or enriched. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

II. Alkene Polymerization Methods

In some embodiments, the organometallic complexes taught in the present application are used in a wide variety of general alkene polymerization methods including gas, slurry, and solution. Such general polymerization methodologies are well known in literature such as those taught in U.S. Pat. Nos. 4,752,597, 6,756,455, and 7,723,450, all of which are incorporated herein by reference. Other general polymerization methodologies are well known in literature including *Handbook of Polymer Synthesis Part A* by Kricheldorf, et al., *Principles of Polymerization* by Odian, and *Advanced Inorganic Chemistry, 5th Edition* by Cotton and Wilkinson, for example, all of which are incorporated herein by reference. In some embodiments and in a slurry polymerization method, the diluent used is an aliphatic or aromatic hydrocarbon solvent or a halogenated version of these solvents. In particular, in some embodiments, one or more of the catalysts described in the present disclosure is used in combination with another catalyst to form a hybrid alkene polymerization catalyst system. Furthermore, the methods described can also be utilized with a hybrid alkene polymerization catalyst system. Additionally, in some embodiments, the methods taught by the present disclosure is optimized to lead to greater polymer production through a higher activity or to achieve specific characteristics of the desired polymers such a plurality of molecular weights or a specific molecular weight. In some embodiments, the polymerization method taught in this application is applied to a wide range of terminal alkenes or aralkenes including but not limited to ethylene, propylene, butylene, or styrene. In some embodiments, the method is optimized for use with ethylene as the monomer feedstock. In some embodiments, these alkene polymerization methods are used in either a batch or continuous reactor. In some embodiments, the reaction additionally contain one or more co-monomers which contain a terminal alkene or a terminal aralkene including but not limited to 1-butene, 1-pentene, 1-hexene, 1-octene, or 1-decene, with the preferred embodiment being 1-butene. In some embodiments, the catalyst and/or the activator are immobilized on a solid support. In some embodiments, such supports include inorganic oxides which are insoluble in the reaction conditions including but not limited to silica, alumina, magnesium oxide, and titanium oxide.

III. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; and "amino" means —NH$_2$. When used in the context of a chemical group: "carboxylate" means a molecule which contains the group, —C(=O)O⁻ (also written as C(O)O⁻ or —CO$_2$⁻) and the overall charge of the molecule is negative or "halide" means a halogen atom formulated as an anion bearing a single negative charge. Any undefined valency on an atom of a structure shown in this application implicitly represents a hydrogen atom bonded to that atom.

In the context of chemical formulas, the symbol "—" means a single bond, "=" means a double bond, and "≡" means triple bond. The symbol "----" represents an optional bond, which if present is either single or double. The symbol "⹀" represents a single bond or a double bond. Thus, for example, the formula

includes

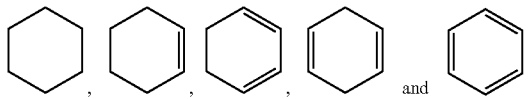

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "▬◣" means a single bond where the group attached to the thick end of the wedge is "out of the page." The symbol "▮▮▮▮" means a single bond where the group attached to the thick end of the wedge is "into the page". The symbol "∿" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M$\equiv$C, each refers to a bond of any type and order between a metal atom and a carbon atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkanes/alkenyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

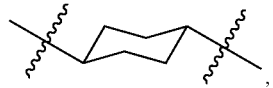 [SMILES: *C1CCC(*)CC1]

are non-limiting examples of alkanediyl groups. It is noted that while the alkenediyl group is aliphatic, once connected at both ends, this group is not precluded from forming an aromatic structure. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

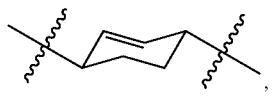

are non-limiting examples of alkenediyl groups. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

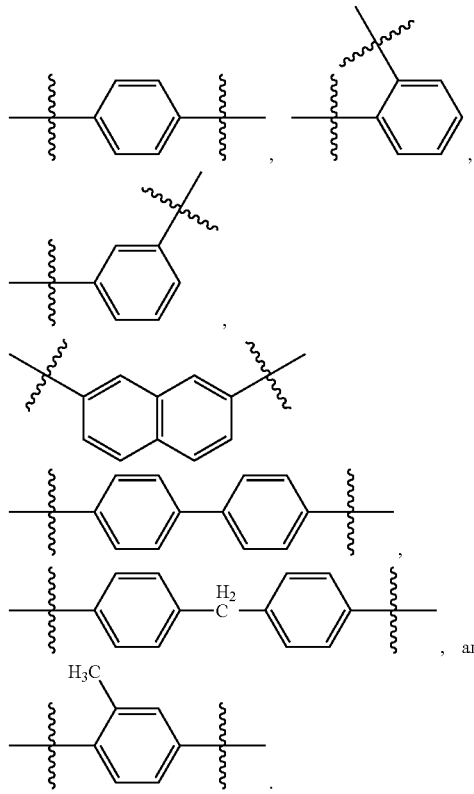

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The term "haloaryl" is a subset of substituted aryl, in which one or more hydrogen atoms has been substituted with a halo group and no other atoms aside from carbon, hydrogen and halogen are present. The group —C₆F₅ is a non-limiting example of a haloaryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "aralkenyl" when used without the "substituted" modifier refers to the monovalent group -alkenediyl-aryl, in which the terms alkenediyl and aryl are each used in a manner consistent with the definitions provided above. Non-limiting examples of aralkenyls are: 2-phenylethenyl (styrene) and 3,3-diphenyl-prop-2-enyl. The term "aralkene" refer to a compound having the formula H—R, wherein R is aralkenyl as this term is defined above. A "terminal aralkene" refers to an aralkene having just one non-aromatic carbon-carbon double bond, wherein that bond forms a vinyl group at one end of the molecule. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkenyls are: (3-nitrophenyl)-ethenyl, and 4-cyano-4-phenyl-but-1-enyl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

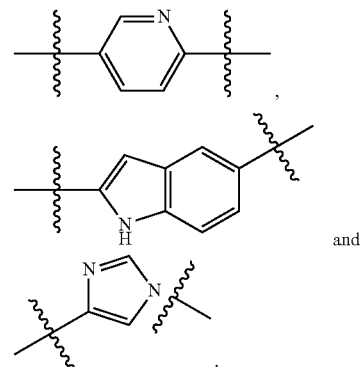

and

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

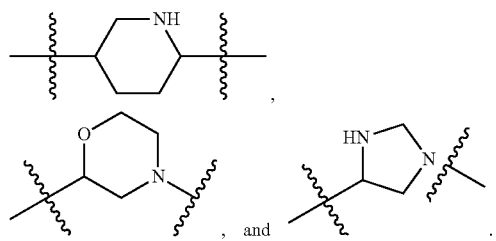

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. When either of these terms are used with the "substituted" modifier one or more hydrogen atom (including a hydrogen atom directly attached the carbonyl, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O— alkanediyl-, —O— alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group. Similarly, the term "ether" corresponds to an alkane, as defined above, wherein at least one of the hydrogen atoms has been replaced with an alkoxy group. Additionally, the addition of the suffix "late" such as in the term "alkoxylate" or "heteroaryloxylate" refers to the group $^-$OR where the oxygen atom has a negative charge and R is defined as appropriate for the prefix using the definitions above.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended.

For example, any method that "comprises," "has" or "includes" one or more steps is not limited to possessing only those one or more steps and also covers other unlisted steps.

The term "hybrid alkene polymerization catalyst system" is defined as a catalyst system comprising one or more late transition metal catalyst, one or more metallocene catalysts, and one or more activating complexes. Additionally, the system may also comprise a solid support for the immobilization of one or more of the late transition metal catalysts, metallocene catalysts, or activating complexes. The late transition metal catalyst may be a catalyst described in U.S. Pat. No. 8,435,911, which is incorporated herein by reference, or other similar polyolefin polymerization catalyst containing a late transition metal. Additionally, the metallocene portion of the catalyst system can be a metallocene described in the present disclosure or any suitable metallocene which has been shown to act as a polyolefin polymerization catalyst. The activating compound could be an aluminoxane or boron containing compound such as borane or boroxines. In particular the aluminoxane could be methyl aluminoxane and contains a cyclic or open chain form such as those described in the present disclosure or in U.S. Pat. No. 8,435,911, which is incorporated herein by reference. The boron containing activator include the activator such as those described in U.S. Pat. No. 8,435,911, WO 05/103096, or WO 97/36937, which are all incorporated herein by reference. Additional activator compounds or complexes include those described in WO 00/31090 or WO 99/06414, both of which are incorporated herein by reference. Furthermore, the solid support could be silica gel, aluminum oxide, mesoporous materials, aluminosilicates, hydrotalcites, organic polymers or polymers containing polar functionalities such as copolymers of ethane and acrylic esters, acrolein, or vinyl acetates. Additionally, the system may comprise an additional organometallic or metallic compound such as those described in WO 05/103096, which is incorporated herein by reference.

An "isomer" of a first compound is a separate compound in which each molecule contains the same constituent atoms as the first compound, but where the configuration of those atoms in three dimensions differs.

A "method" is series of one or more steps undertaking lead to a final product, result or outcome. As used herein, the word "method" is used interchangeably with the word "process".

The above definitions supersede any conflicting definition in any reference that is incorporated by reference herein. The fact that certain terms are defined, however, should not be considered as indicative that any term that is undefined is indefinite. Rather, all terms used herein are believed to describe the embodiments disclosed herein in terms such that one of ordinary skill can appreciate the scope and practice of the embodiments disclosed herein.

V. Examples

The following examples are included to demonstrate preferred embodiments of the disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Novel Substituted Zirconocenes

Complex 11:

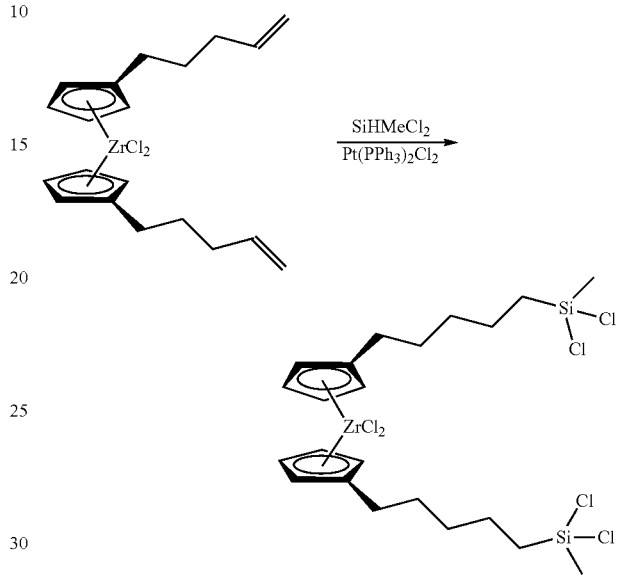

$Pt(PPh_3)_2Cl_2$ (57 mg, 72 mmol) was added to solution of complex 338 (1.03 g, 2.4 mmol) and $SiHMeCl_2$ (1.15 g, 10 mmol) in toluene (25 mL). The mixture was heated with stirring at 60° C. for 6 h, and 16 h at room temperature. The solvent was removed under reduced pressure, the residue was recrystallized from pentane yielding 0.59 g (37%) of the product.

$^1H$ NMR ($CDCl_3$): δ 6.30 (t, 4H); 6.20 (t, 4H); 2.64 (t, 4H); 1.61-1.40 (m, 12H); 1.12 (m, 4H); 0.76 (s, 6H).

$^{13}C$ NMR ($CDCl_3$): δ 134.84; 116.74; 112.06; 31.94; 30.01; 29.89; 22.18; 21.47; 5.18.

Complex 12:

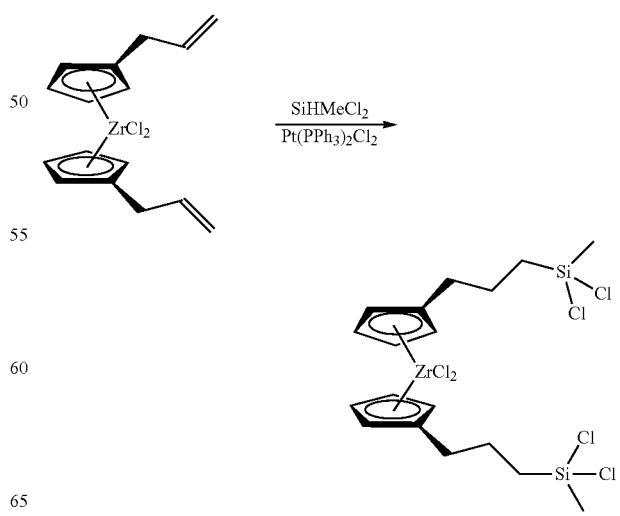

Pt(PPh$_3$)$_2$Cl$_2$ (60 mg, 75 mmol) was added to solution of complex 332 (0.56 g, 1.5 mmol) and SiHMeCl$_2$ (0.6 g, 6 mmol) in toluene (15 mL). The mixture was heated with stirring at 60° C. for 6 h, and 16 h at room temperature. The solvent was removed under reduced pressure, the residue was recrystallized from pentane yielding 0.56 g (64%) of the product.

$^1$H NMR (CDCl$_3$): δ 6.32 (m, 4H); 6.23 (m, 4H); 2.73 (t, 4H); 1.77 (m, 4H); 1.14 (m, 4H); 0.77 (s, 6H).

$^{13}$C NMR (CDCl$_3$): δ 133.75; 117.02; 112.10; 32.61; 23.73; 21.28; 5.18.

Complex 18:

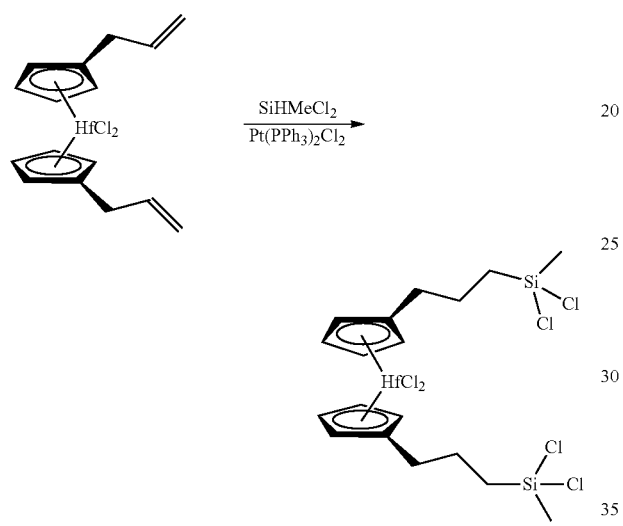

Pt(PPh$_3$)$_2$Cl$_2$ (35 mg, 44 mmol) was added to solution of complex 335 (1.01 g, 2.2 mmol) and SiHMeCl$_2$ (0.76 g, 6.6 mmol) in toluene (20 mL). The mixture was heated with stirring at 60° C. for 6 h, and 16 h at room temperature. The solvent was removed under reduced pressure, and the residue was recrystallized from pentane yielding 0.79 g (52%) of the product.

$^1$H NMR (CDCl$_3$): δ 6.22 (m, 4H); 6.12 (m, 4H); 2.75 (t, 4H); 1.77 (m, 4H); 1.14 (m, 4H); 0.77 (s, 6H).

$^{13}$C NMR (CDCl$_3$): δ 131.62; 115.58; 110.80; 32.51; 23.93; 21.30; 5.17.

Complex 20:

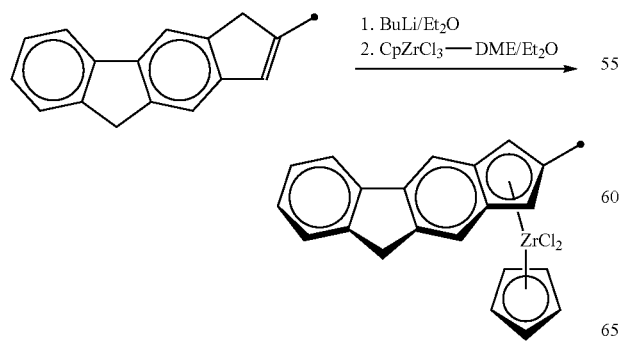

(1,2,3,3a,10a-η$^5$-2-methyl-3,9-dihydrocyclopenta[b]fluorenyl)(η$^5$-cyclopentadienyl)dichlorozirconium (IV)

n-BuLi (1.6M solution in hexane, 9.4 ml, 15 mmol) was added to cooled (−40° C.) solution of 2-methyl-3,9-dihydrocyclopenta[b]fluorene in Et$_2$O (40 ml). The mixture was allowed to warm to room temperature, stirred for 3 h, cooled to −40° C., and CpZrCl$_3$(DME) (5.29 g, 15 mmol) was added. Resulting mixture was allowed to warm to room temperature, stirred for 16 h, and filtered. Resulting precipitate was recrystallized from CH$_2$Cl$_2$-pentane (1:1). The yield 2.46 g (37%), yellow crystalline powder.

$^1$H NMR (CDCl$_3$, 20° C.) δ: 2.38 (s, 3H, —CH$_3$); 4.05 (AB, 2H, $^2$J=22 Hz, —CH$_2$—); 6.04 (s, 5H, C$_5$H$_5$); 6.30 (s, 1H); 6/35 (s, 1H) {—CH═}; 7.35-7.44 (m, 2H); 7.55 (d, $^3$J=7.3 Hz, 1H); 7.74 (s, 1H); 7.88 (d, $^3$J=7.1 Hz); 7.96 (s, 1H) {C$_{Ar}$—H}.

$^{13}$C NMR (CDCl$_3$, 20° C.) δ: 17.5; 36.2; 104.1; 104.4; 114.4; 116.4; 120.5; 120.7; 125.4; 125.9; 127.2; 128.2; 133.9; 140.1; 140.4; 141.6; 143.5.

Complex 21:

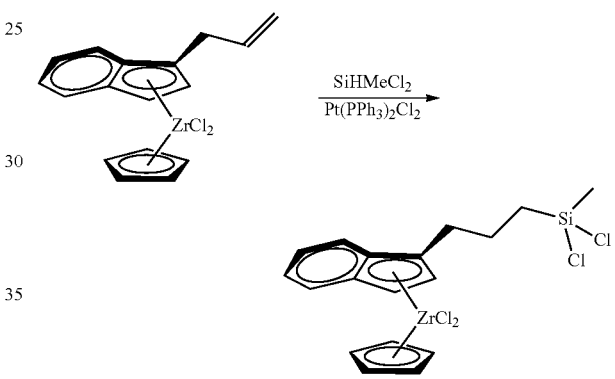

Prepared by procedure used for Complex 24.

$^1$H NMR (CDCl$_3$): δ 7.65 (m, 2H); 7.29 (m, 2H); 6.69 (bs, 1H); 6.48 (bs, 1H); 6.15 (s, 5H); 3.14 (m, 1H); 2.98 (m, 1H); 1.87 (m, 2H); 1.20 (m, 2H); 0.77 (s, 3H).

$^{13}$C NMR (CDCl$_3$): δ 126.40; 126.05; 125.52; 125.49; 124.85; 124.41; 123.88; 121.21; 120.67; 30.43; 21.46; 5.18.

Complex 24:

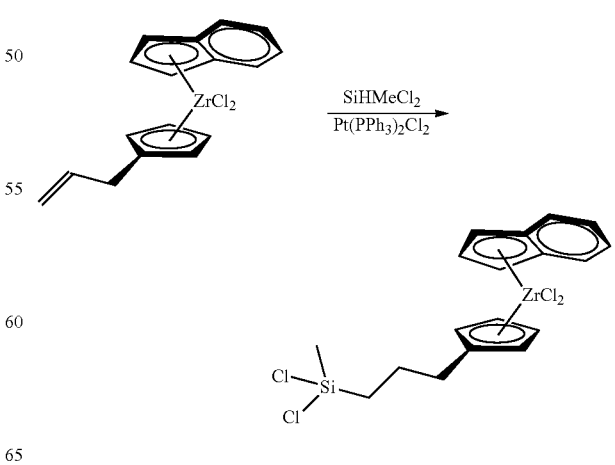

Pt(PPh$_3$)$_2$Cl$_2$ (31 mg, 40 mmol) was added to solution of (Ind)(AllylCp)ZrCl$_2$ (0.79 g, 2 mmol) and SiHMeCl$_2$ (0.46 g, 4 mmol) in toluene (15 mL). The mixture was heated with stirring at 60° C. for 6 h, and 16 h at room temperature. The solvent was removed under reduced pressure, the residue was recrystallized from pentane yielding 0.44 g (44%) of the product.

$^1$H NMR (CDCl$_3$): δ 7.70 (m, 2H); 7.32 (m, 2H); 6.94 (t, 1H); 6.54 (m, 2H); 5.96 (bs, 2H); 5.89 (bs, 2H); 2.62 (t, 2H); 1.69 (m, 2H); 1.09 (m, 2H); 0.76 (s, 3H).

Complex 25:

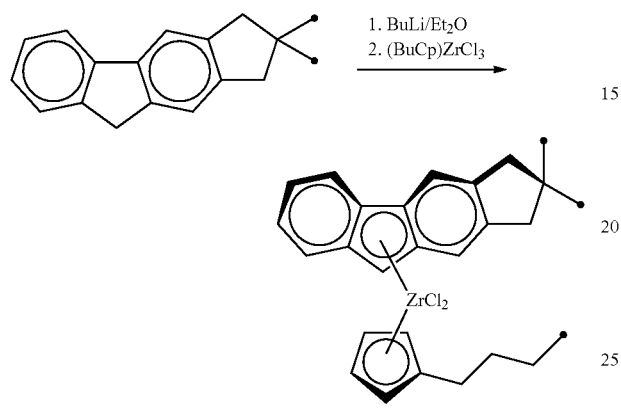

($\eta^5$-butylcyclopentadienyl)($\eta^5$-2,2-dimethyl-1,2,3,9-tetrahydrocyclopenta[b]fluorenyl)dichlorozirconium (IV)

n-BuLi (2.5M solution in hexane, 2.1 ml, 5.2 mmol) was added to cooled (−40° C.) solution of 2,2-dimethyl-1,2,3,9-tetrahydrocyclopenta[b]fluorene (1.17 g, 5 mmol) in Et$_2$O (40 ml). The mixture was allowed to warm to room temperature, stirred for 3 h, cooled to −40° C., and (BuCp)ZrCl$_3$×DME (2.13 g, 5.2 mmol) was added. The mixture was allowed to warm to room temperature and stirred for 16 h. TMEDA (1.5 ml, ~10 mmol) was added, and the mixture was filtered. Yellow precipitate was washed by ether (20 ml) and pentane (30 ml). The product was recrystallized (hexane-toluene, 1:3) and dried in vacuo. The yield 0.86 g (33%).

$^1$H NMR (CDCl$_3$, 20° C.) δ: 0.87 (t, 3J=7.3 Hz, 3H); 1.16 (s, 3H); 1.21 (s, 2H); 1.27 (m, 2H); 1.42 (m, 2H) 2.80 (br., 2H); 2.84 (d, 1H, $^2$J=15.7 Hz); 2.96 (d, 1H, $^2$J=15.7 Hz); 5.84-5.96 (m, 4H, Cp ring); 6.43 (s, 1H); 7.26-8.07 (group of m, 5H, C$_{Ar}$—H).

Complex 26:

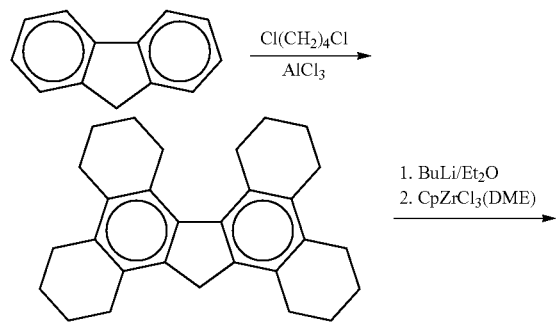

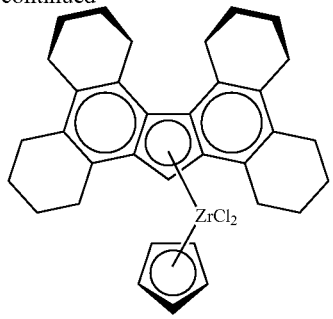

9,9'-methylene-10,10'-bi(1,2,3,4,5,6,7,8-octahydrophenanthrenyl) or hexadecahydrotetrabenzo[a,c,d,f]fluorene Fluorene (12.5 g, 75.2 mmol) was dissolved in 1,4-dichlorobutane (76.4 g, 602 mmol). Clear solution was cooled with stirring to −20° C., and AlCl$_3$ (5.0 g, 37.6 mmol) was added. Reaction mixture was allowed to warm to room temperature, stirred for 16 h at 20° C. and 72 h at 60-80° C., poured into ice/HCl. Organic layer was separated, aqueous layer was extracted by CHCl$_3$ (350 ml). Combined organic phase was washed by water, Na$_2$CO$_3$, dried over Na$_2$SO$_4$ and evaporated. Ether (150 ml) was added, after 16 h yellow precipitate was filtered off and dried in vacuo. The yield 3.45 g (12%).

$^1$H NMR (CDCl$_3$, 20° C.) δ: 1.70 (br., 4H); 1.92 (br, 12H); 2.70-2.85 (group of br., 12H); 3.09-3.22 (br, 4H); 3.54 (s, 2H).

$^{13}$C NMR (CDCl$_3$, 20° C.) δ: 22.6; 23.31; 23.34; 23.5; 26.8; 27.0; 27.1; 33.3; 34.6; 129.8; 130.6; 133.6; 133.7; 139.6; 139.9.

Complex 30:

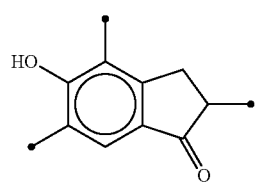

5-Hydroxy-2,4,6-trimethylindan-1-one

Solution of 2,6-dimethylphenol (36.65 g, 0.3 mol) in CH$_2$Cl$_2$ (100 ml) was added to well stirred suspension of AlCl$_3$ (120 g, 0.9 mol) in CH2Cl2 (200 ml). After 20 min, 2-bromoisobutyryl bromide (69 g, 0.3 mol) was added. Reaction mixture was stirred for 3 days, poured into HCl/crashed ice, organic phase was separated, water phase was extracted by CH$_2$Cl$_2$ (3×100 ml), combined organic fraction was washed by water, dried over MgSO$_4$, and evaporated. Ether (70 ml) and hexane (70 ml) were added, resulting crystalline precipitate was filtered off and dried in vacuo. The yield 15.8 g (27.7%).

NMR $^1$H (CDCl$_3$) δ: 7.45 (s, 1H); 6.05 (broad, 1H); 3.25 (dd, 1H); 2.69 (m, 1H); 2.54 (dd, 1H); 2.29 (s, 3H); 2.22 (s, 3H); 1.30 (d, 3H).

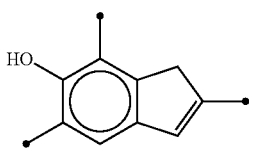

2,5,7-Trimethyl-1H-inden-6-ol

Suspension of 5-hydroxy-2,4,6-trimethylindan-1-one (4.74 g, 24.9 mmol) in THF (30 ml) was added at 0° C. to suspension of LiAlH$_4$ (0.94 g, 24.9 mmol) in THF (50 ml). The mixture was allowed to warm to room temperature, stirred for 2 h. 5% HCl (20 ml) was added, resulting mixture was extracted by CH$_2$Cl$_2$ (4×50 ml), combined organic fraction was washed by water, dried over MgSO$_4$, passed through silica gel, and evaporated. Residue was washed by cold pentane and dried in vacuo. The yield 3.75 g (86%).

NMR $^1$H (CDCl$_3$) δ: 6.88 (s, 1H); 6.37 (s, 2H); 4.47 (broad s, 1H); 3.16 (s, 2H); 2.26 (s, 3H); 2.23 (s, 3H); 2.12 (s, 3H).

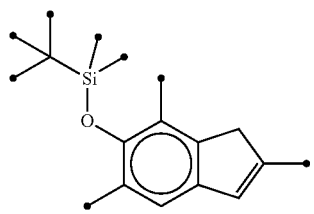

tert-Butyl(dimethyl)[(2,5,7-trimethyl-1H-inden-6-yl)oxy]silane

Mixture of 2,5,7-trimethyl-1H-inden-6-ol (1.8 g, 10.3 mmol), imidazole (1.76 g, 25.8 mmol), and tert-butylchlorodimethylsilane (1.87 g, 12.4 mmol) in CH$_3$CN (35 ml) was stirred for 16 h at room temperature, poured into 2% HCl (100 ml), extracted by pentane (4×20 ml). Combined organic fraction was washed by water, dried over MgSO4, and evaporated. The yield 2.8 g (94%).

NMR $^1$H (CDCl$_3$) δ: 6.89 (s, 1H); 6.38 (s, 2H); 3.14 (s, 2H); 2.24 (s, 3H); 2.19 (s, 3H); 2.13 (s, 3H), 1.06 (s, 9H); 0.19 (s, 6H).

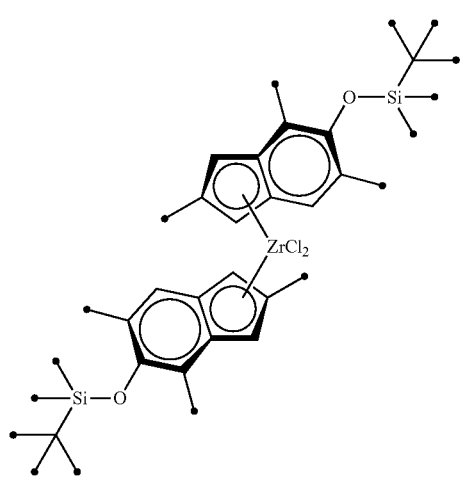

Bis(η$^5$-2,5,7-trimethyl-6-tert-butyldimethylsiloxy-1H-indenyl)dichlorozirconium (IV)

BuLi (1.6M in hexane, 2.1 ml, 3.3 mmol) was added at −20° C. to the solution of tert-butyl(dimethyl)[(2,5,7-trimethyl-1H-inden-6-yl)oxy]silane (0.87 g, 3 mmol) in Et$_2$O (25 ml). Reaction mixture was allowed to warm to room temperature, stirred for 1 h, cooled to −40° C., ZrCl$_4$ (0.37 g, 1.6 mmol) was added. Reaction mixture was stirred for 2 h at −40° C., allowed to warm to room temperature, stirred for 16 h. The solution was separated by decantation, evaporated, the residue was recrystallized from hexane. The yield 0.48 g (43%), yellow crystalline powder.

NMR $^1$H (CDCl$_3$) for mixture of isomers δ: 7.25 (s, 2H); 6.14 (s, 2H); 5.85 (s, 2H); 2.28 (s, 6H); 2.27 (s, 6H); 2.24 (s, 6H); 1.07 (s, 18H); 0.15 (s, 12H), and 6.98 (s, 2H); 6.21 (s, 2H); 6.05 (s, 2H); 2.34 (s, 6H); 2.24 (s, 6H); 1.93 (s, 6H); 1.07 (s, 18H); 0.27 (s, 6H); 0.21 (s, 6H).

Complex 32:

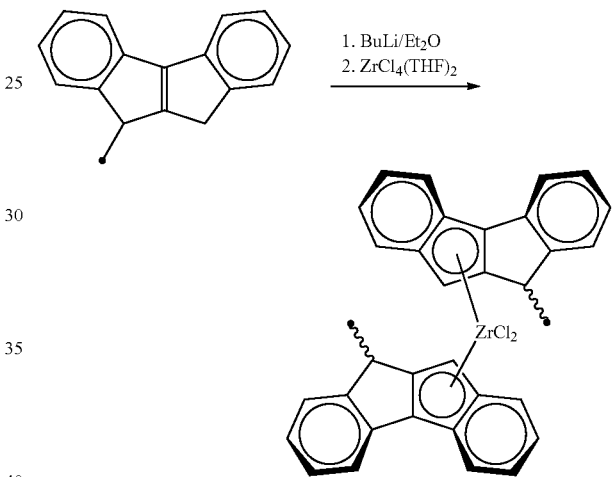

Bis-(5a,6,6a,10a,10b-η$^5$-5-methyl-5,6-dihydroindeno[1,2-α]indenyl)dichlorozirconium (IV)

n-BuLi (2.5M, 6.1 ml, 15.2 mmol) was added at −40° C. to solution of 5-methyl-5,6-dihydroindeno[1,2-a]indene (3.27 g, 15 mmol) in Et$_2$O (50 ml). The mixture was allowed to warm to room temperature, stirred for 3 h, cooled to −20° C., and ZrCl$_4$(THF)$_2$ (2.86 g, 7.6 mmol) was added. After 16 h of stirring, the precipitate was filtered off, washed by Et$_2$O, pentane and recrystallized from toluene. The yield 1.06 g (24%).

$^1$H NMR (CDCl$_3$, 20° C.) δ: 1.18 (d); 1.34 (d) {3H, —CH$_3$}; 3.19 (q); 3.30 (q) {1H}; 6.02 (s); 6.24 (s) {1H}; 6.80-7.96 (groups of m, 16H).

Complex 48:

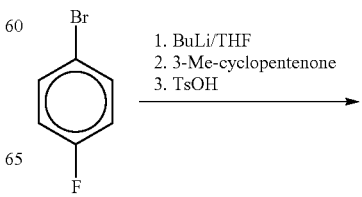

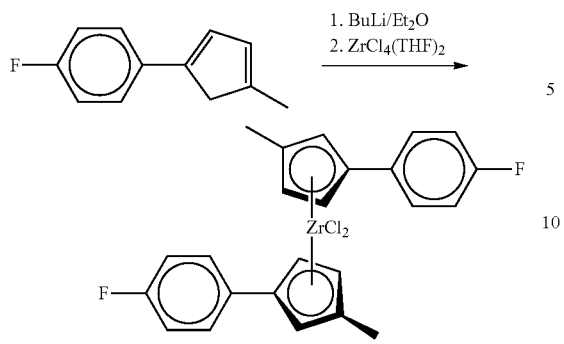

1-Fluoro-4-(4-methyl-1,4-cyclopentadien-1-yl)benzene

The solution of 1-bromo-4-fluorobenzene (26.3 g, 150 mol) in 200 mL of Et$_2$O was cooled to −50° C. and BuLi (94 mL, 1.6 M in hexane, 150 mmol) was added. The mixture was stirred at this temperature for 40 min and warmed to 0° C. Then the solution of 3-methylcyclopenen-2-one (14.4 g, 150 mmol) in 15 mL of ether was added and mixture was stirred overnight. Water (30 mL) was added. The organic layer was separated, washed by brine and concentrated to 100 mL. TsOH (0.5 g) was added and mixture was refluxed for 1 min. After cooling mixture was washed by 5% NaHCO$_3$, brine, dried over MgSO$_4$, solvent was evaporated and residue was recrystallized from methanol. The yield was 10.5 g (40%).

$^1$H NMR (CDCl$_3$): δ 7.48 (m, 2H); 7.05 (m, 2H); 6.70-6.04 (m, 2H); 3.45 (m, 2H); 2.09 (s, 3H).

1-Fluoro-4-(4-methyl-1,4-cyclopentadien-1-yl)benzene (7 g, 40 mmol) was dissolved in mixture of 50 mL of THF and 30 mL of hexane, cooled to −40° C. and treated with BuLi (25 mL, 1.6 M in hexane, 40 mmol). Mixture was stirred at this temperature for 2 h, and warmed to 0° C. The resulting solution was cooled to −70° C. and ZrCl$_4$(THF)$_2$ (7.5 g, 20 mmol) was added. The mixture was stirred overnight at room temperature, filtered, and the filtrate was evaporated. The residue was treated by mixture of hexane (60 mL) and dichloromethane (15 mL). Precipitate was filtered off, washed with pentane and dried. The yield was 6.2 g (62%).

$^1$H NMR (CDCl$_3$): δ 7.40 (m, 4H); 7.10 (m, 4H); 6.48 (t, 1H); 6.43 (t, 1H); 6.38 (t, 1H); 6.33 (t, 1H); 5.84 (m, 2H); 2.16 (s, 3H); 2.11 (s, 3H).

Complex 50:

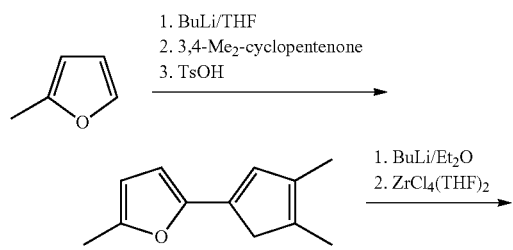

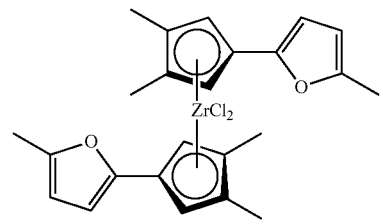

2-(3,4-Dimethyl-1,3-cyclopentadien-1-yl)-5-methylfuran

The solution of 2-methylfurane (9 mL, 100 mmol) in 120 mL THF was cooled to 0° C., and BuLi (50 mL, 1.6 M in hexane, 80 mmol) was added dropwise. After 1.5 h the solution of 3,4-dimethylcyclopenen-2-one (8.8 g, 80 mmol) in 10 mL of ether was added at the same temperature. After 16 h of stirring, water (2 mL) was added, solution was separated from precipitate and precipitate was washed by 20 mL of ether. TsOH (0.5 g) was added to combined solution, the mixture was heated to reflux, cooled, washed by NaHCO$_3$, brine, dried over MgSO$_4$ and evaporated. Residue was distilled in vacuo (B. p. 75-77° C./0.8 torr), yielding the product (8.3 g, 60%).

$^1$H NMR (CDCl$_3$): δ 6.48 (s, 1H); 6.11 (d, 1H); 5.96 (m, 1H); 3.21 (s, 2H); 2.33 (s, 3H); 1.97 (s, 3H); 1.90 (d, 3H).

Solution of 2-(3,4-dimethyl-1,3-cyclopentadien-1-yl)-5-methylfuran (4.2 g, 24 mmol) in Et$_2$O (40 mL) was cooled to 0° C. and BuLi (15 mL, 1.6 M in hexane, 24 mmol) was added dropwise. Mixture was stirred for 2 h at room temperature, cooled again, and ZrCl$_4$(THF)$_2$ (4.5 g, 12 mmol) was added. The mixture was stirred overnight, filtered, the filtrate was evaporated. The residue crystallizes slowly. Solid product was washed with pentane and dried. The yield was 2.8 g (46%).

$^1$H NMR (CDCl$_3$): δ 6.36 (s, 4H); 6.28 (d, 2H); 6.07 (d, 2H); 2.43 (s, 6H); 1.84 (s, 12H).

Complex 51:

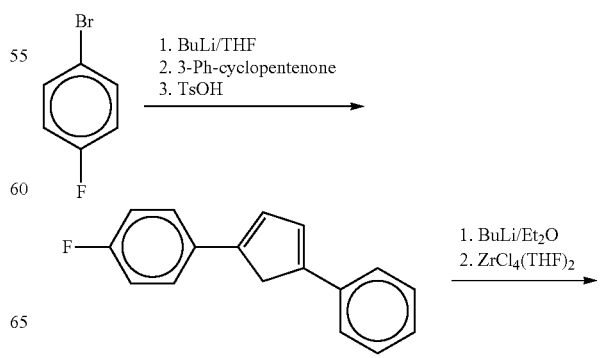

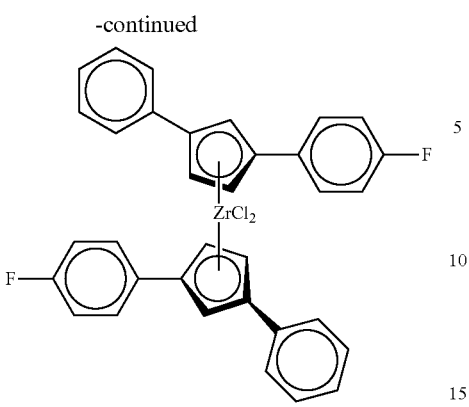

1-Fluoro-4-(4-methyl-1,4-cyclopentadien-1-yl)benzene

The solution of 1-bromo-4-fluorobenzene (8.75 g, 50 mol) in 100 mL of Et$_2$O was cooled to −50° C. and BuLi (32 mL, 1.6 M in hexane, 50 mmol) was added dropwise, the mixture was stirred at this temperature for 40 min and warmed to 0° C. The solution of 3-phenyl-cyclopenene-2-on (7.9 g, 50 mmol) in 40 mL of THF was added and mixture was stirred overnight. Mixture was treated by 30 mL of 10% NH$_4$Cl, and then organic layer was separated and washed by brine. Then TsOH (0.5 g) was added, the mixture was refluxed for 1 min. After cooling the mixture was washed by 5% NaHCO$_3$, brine, dried over MgSO$_4$. Solvent was evaporated, and the residue was recrystallized (ethanol), yielding 6.8 g of the product as a mixture of isomers (58%).

$^1$H NMR (CDCl$_3$): δ 7.61 (m, 4H); 7.40 (m, 2H); 7.26 (m, 2H); 7.09 (m, 2H), 6.65 (m, 1H); 6.60 (m, 1H); 3.60 (d, 2H).

The solution of 1-fluoro-4-(4-methyl-1,4-cyclopentadien-1-yl)benzene (3 g, 12.7 mmol) in Et$_2$O (40 mL) was cooled to 0° C., and BuLi (8 mL, 1.6 M in hexane, 13 mmol) was added dropwise. Mixture was stirred for 2 h at room temperature, cooled again to 0° C., and ZrCl$_4$(THF)$_2$ (2.4 g, 6.3 mmol) was added. After 16 h of stirring, the yellow precipitate was filtered off, dissolved in dichloromethane, and solvent was evaporated. Residue was extracted by toluene-hexane mixture (3:1, 70 mL). Solvent was evaporated, and the residue was dried in vacuo. The yield was 1.7 g (1:1 mixture of isomers).

$^1$H NMR (CDCl$_3$): δ 7.42 (m, 14H); 7.02 (m, 6H); 6.35 (m, 2H); 6.27 (m, 2H).

Complex 52:

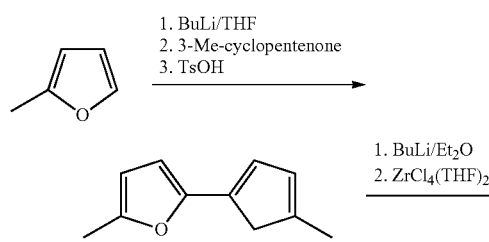

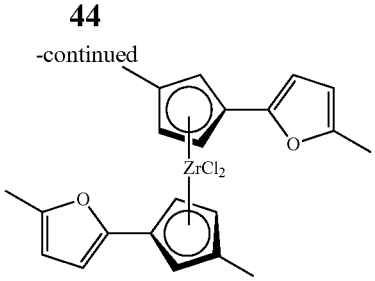

2-Methyl-5-(4-methyl-1,4-cyclopentadien-1-yl)furan

The solution of 2-methylfuran (8.2 g, 100 mmol) in 120 mL of abs. THF was cooled to 0° C. and BuLi (50 mL 2.5N in hexane, 80 mmol) was added dropwise and stirred at this temperature for 1.5 h. The solution of 3-methylcyclopenen-2-one (7.7 g, 80 mmol) in 10 mL of THF was added and mixture was stirred overnight. Mixture was treated by 3 mL of water, organic layer was separated. TsOH (0.5 g) was added, and the mixture was refluxed for 1 min. After cooling the mixture was washed by 5% NaHCO$_3$, brine, dried over MgSO$_4$, solvent was evaporated and residue was distilled in vacuo, yielding 6.5 g of product as mixture of 3 isomers (yield 50%, b.p. 70-71° C./1 torr).

$^1$H NMR (CDCl$_3$): δ 6.57 (s, 1H); 6.22 (d, 1H); 5.99 (m, 1H); 5.91 (m, 1H); 3.28 (s, 2H); 2.35 (s, 3H); 2.04 (s, 3H).

The solution of 2-(3,4-dimethyl-1,3-cyclopentadien-1-yl)-5-methylfuran (3.2 g, 20 mmol) in Et$_2$O (40 mL) was cooled to −20° C. and BuLi (8 mL 2.5N in hexane, 20 mmol) was added dropwise. Suspension obtained was stirred 1 h at room temperature, cooled again to −20° C., and ZrCl$_4$(THF)$_2$ (3.77 g, 10 mmol) was added. After 16 h of stirring, the precipitate was filtered off, dissolved in dichloromethane, solution was filtered and solvent was evaporated. Residue was washed with Et$_2$O, pentane and dried in vacuo giving 0.6 g of product as pure form. Filtrate was concentrated and 1.3 g of complex was obtained as mixture of isomers (1:1 ratio). (total yield 38%).

$^1$H NMR (CDCl$_3$): δ(for pure form) 6.51 (s, 2H); 6.37 (s, 2H); 6.32 (s, 2H); 6.05 (s, 2H); 5.83 (s, 2H); 2.40 (s, 6H); 2.07 (s, 6H).

Complex 54:

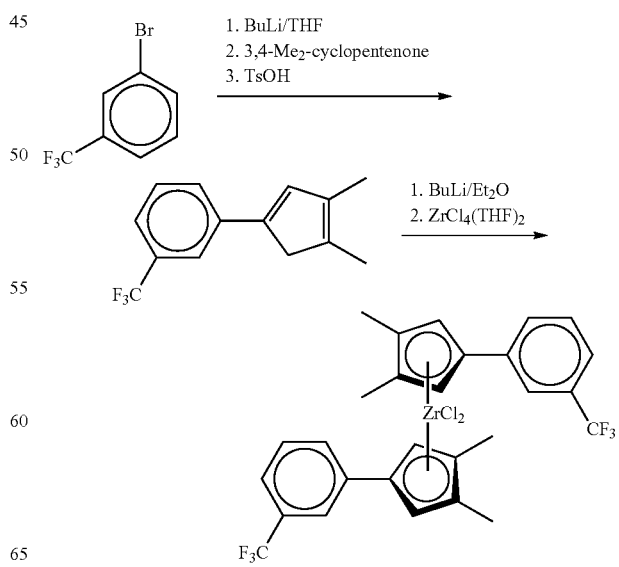

1-(3,4-Dimethyl-1,3-cyclopentadien-1-yl)-3-trifluoromethylbenzene

The solution of 1-bromo-3-(trifluoromethyl)lbenzene (22.5 g, 50 mmol) in 150 mL of Et$_2$O was cooled to −70° C., and BuLi (63 mL, 1.6 M in hexane, 100 mmol) was added. The mixture was stirred at this temperature for 2 h, 3,4-dimethylcyclopenen-2-one (11 g, 100 mmol) in 50 mL of ether was added, the mixture was stirred overnight, and treated by 30 mL of water. Organic layer was separated and washed by brine. TsOH (0.5 g) was added, and the mixture was refluxed for 3 min. After cooling the mixture was washed by 5% NaHCO$_3$, brine, dried over MgSO$_4$, solvent was evaporated and residue was distilled in vacuo, (b.p. 95-97° C./1 torr) yielding 14 g (59%) of the product.

$^1$H NMR (CDCl$_3$): δ 7.66 (br.s, 1H); 7.57 (m, 1H); 7.37 (m, 2H), 6.74 (br.s, 1H); 3.26 (s, 2H); 1.99 (s, 3H); 1.91 (d, 3H).

The solution of 1-(3,4-dimethyl-1,3-cyclopentadien-1-yl)-3-(trifluoromethyl)benzene (4.76 g, 20 mmol) in Et$_2$O (40 mL) was cooled to −30° C., and BuLi (12.5 mL, 1.6 M in hexane, 20 mmol) was added dropwise. The mixture was stirred 2 h at room temperature, cooled again to −30° C., and ZrCl$_4$(THF)$_2$ (3.77 g, 10 mmol) was added. After 16 h of stirring, precipitate was filtered off, dissolved in dichloromethane, solution was filtered and evaporated. Residue was washed with pentane and dried in vacuo. The yield was 4 g (63%).

$^1$H NMR (CDCl$_3$): δ 7.65 (s, 2H); 7.56 (m, 6H); 6.21 (s, 4H); 1.81 (s, 12H).
Complex 55

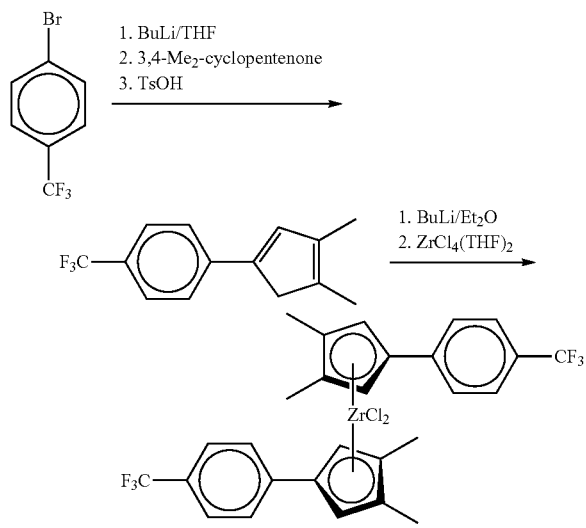

1-(3,4-Dimethyl-1,3-cyclopentadien-1-yl)-4-trifluoromethylbenzene

The solution of 1-bromo-4-(trifluoromethyl)lbenzene (11.25 g, 50 mmol) in 80 mL of Et$_2$O was cooled to −50° C., and BuLi (32 mL, 1.6 M in hexane, 50 mmol) was added. The mixture was stirred at this temperature for 40 min, and 3,4-dimethylcyclopenen-2-one (5.5 g, 50 mmol) in 10 mL of ether was added. After 16 h of stirring, the mixture was treated by 30 mL of water, organic layer was separated and washed by brine. TsOH (0.5 g) was added, and the mixture was refluxed for 1 min. After cooling the mixture was washed by 5% NaHCO$_3$, brine, dried over MgSO$_4$, solvent was evaporated and the residue was recrystallized from methanol, yielding 8.5 g (71.4%) of the product.

$^1$H NMR (CDCl$_3$): δ 7.56 (m, 4H); 6.84 (s, 1H); 3.33 (s, 2H); 2.06 (s, 3H); 1.97 (s, 3H).

The solution of 1-(3,4-dimethyl-1,3-cyclopentadien-1-yl)-4-(trifluoromethyl)benzene (4.76 g, 20 mmol) in Et$_2$O (40 mL) was cooled to −30° C., and BuLi (12.5 mL, 1.6 M in hexane, 20 mmol) was added dropwise. Mixture was stirred 2 h at room temperature, cooled again to −30° C., and ZrCl$_4$(THF)$_2$ (3.77 g, 10 mmol) was added. After 16 h of stirring, precipitate was filtered off and extracted by hot benzene. Solvent was evaporated, and the residue was washed by pentane and dried in vacuo. The yield was 3.1 g (48%).

$^1$H NMR (CDCl$_3$): δ 7.70 (d, 4H); 7.55 (d, 4H); 6.34 (s, 4H); 1.84 (s, 12H).
Complex 56:

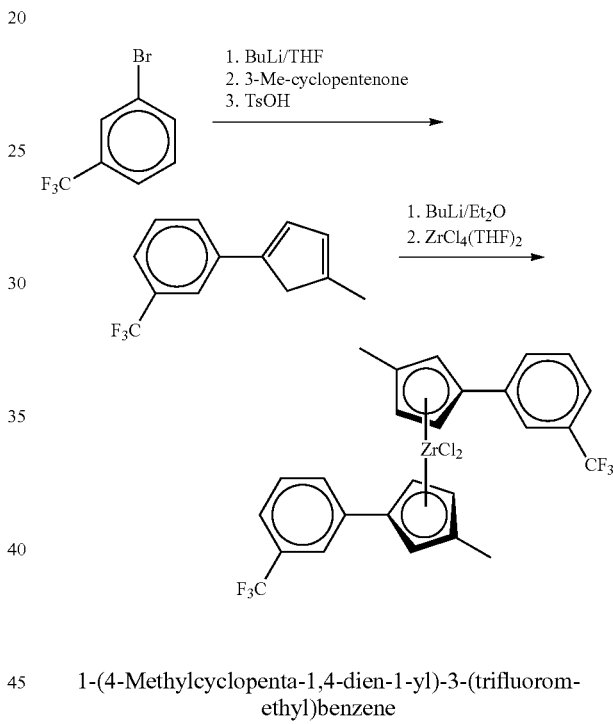

1-(4-Methylcyclopenta-1,4-dien-1-yl)-3-(trifluoromethyl)benzene

The solution of 1-bromo-3-(trifluoromethyl)benzene (22.5 g, 100 mmol) in 200 mL of Et$_2$O was cooled to −50° C., and BuLi (63 mL, 1.6 M in hexane, 100 mmol) was added. The mixture was stirred at this temperature for 1 h. The solution of 3-methylcyclopenen-2-one (9.6 g, 100 mmol) in 20 mL of ether was added and mixture was stirred overnight. Mixture was treated by 20 mL of water, organic layer was separated and washed by brine. TsOH (0.5 g) was added, and the mixture was refluxed for 1 min. After cooling the mixture was washed by 5% NaHCO$_3$, brine, dried over MgSO$_4$, solvent was removed, and the residue was recrystallized from methanol, yielding 14.6 g (65%) of the product.

$^1$H NMR (CDCl$_3$): δ 7.81-7.39 (group m, 4H, Aryl); 6.85 (bs); 6.55 (bs); 6.22 (bs); 6.08 (bs) {2H, —CH=}; 3.36 (bs); 3.29 (bs); 3.12 (bs) {2H, —CH$_2$-}; 2.16 (m), 2.14 (m), 2.07 (m) {3H, —CH$_3$}.

The solution of 1-(4-methyl-1,4-cyclopentadien-1-yl)-3-(trifluoromethyl)benzene (4.5 g, 20 mmol) in Et$_2$O (40 mL) was cooled to −30° C., and BuLi (12.5 mL, 1.6 M in hexane, 20 mmol) was added dropwise. Mixture was stirred for 2 h at room temperature, cooled to 0° C., and $ZrCl_4(THF)_2$ (3.7 g, 10 mmol) was added. After 16 h of stirring, the reaction mixture was filtered, filtrate was evaporated. Liquid residue was treated with pentane and was stated for 2 days. Yellow precipitate was filtered off and dried in vacuo. The yield was 2 g (33%).

$^1$H NMR ($CDCl_3$): δ 7.61 (m, 4H); 7.47 (m, 4H); 6.58 (m, 2H); 6.44 (m, 2H); 5.94 (m, 2H); 2.18 (s, 6H).

Complex 57 (57a—Minor Isomer, 57b—Major Isomer)

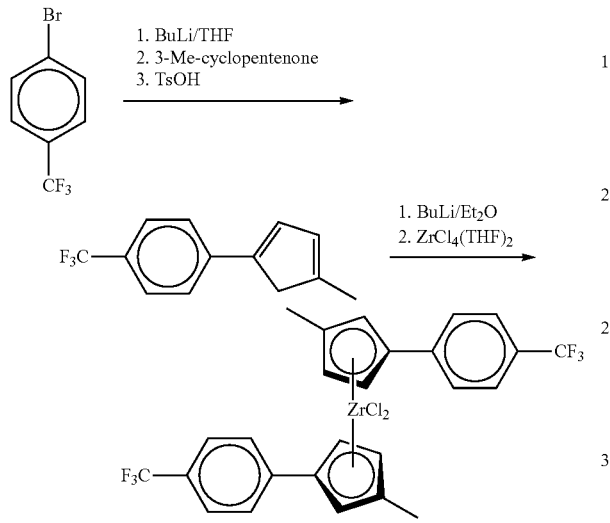

1-(4-Methylcyclopenta-1,4-dien-1-yl)-4-(trifluoromethyl)benzene

The solution of 1-bromo-4-(trifluoromethyl)benzene (13.8 g, 61 mmol) in 100 mL of $Et_2O$ was cooled to −50° C., and BuLi (38 mL, 1.6 M in hexane, 61 mmol) was added. The mixture was stirred at this temperature for 1 h. The solution of 3-methylcyclopenen-2-one (5.8 g, 61 mmol) in 10 mL of ether was added and mixture was stirred overnight. The mixture was treated by 20 mL of water, organic layer was separated and washed by brine. TsOH (0.5 g) was added, and the mixture was refluxed for 1 min. After cooling the mixture was washed by 5% $NaHCO_3$, brine, dried over $MgSO_4$, solvent was removed, and the residue was recrystallized from methanol, yielding 4.3 g of product (32%).

$^1$H NMR ($CDCl_3$): δ 7.62-7.52 (group m, 4H, Aryl); 6.86 (bs); 6.09 (bs) {2H, —CH═}; 3.35 (bs, 2H, —$CH_2$—); 2.05 (bs, 3H, —$CH_3$).

The solution of 1-(4-methyl-1,4-cyclopentadien-1-yl)-4-(trifluoromethyl)benzene (4.3 g, 19 mmol) in $Et_2O$ (40 mL) was cooled to −30° C., and BuLi (12 mL, 1.6 M in hexane, 19 mmol) was added dropwise. Mixture was stirred 1 h at room temperature, cooled to 0° C., and $ZrCl_4(THF)_2$ (3.4 g, 9 mmol) was added. After 16 h of stirring, reaction mixture was filtered, precipitate was washed with ether, filtrate was evaporated, residue was washed with pentane, yielding 2.2 g of complex as mixture of isomers, 57a and 57b (57b is the main isomer). Insoluble residue at filter was treated with dichloromethane, precipitate of LiCl was separated by centrifuge, solvent was evaporated, residue was washed with ether yielding 1.5 g of complex 57 (containing 57 a and 57b).

Complex 57b $^1$H NMR ($CDCl_3$): δ 7.62 (d, 4H); 7.49 (d, 4H); 6.54 (m, 2H); 6.48 (m, 2H); 5.89 (m, 2H); 2.15 (s, 6H).

Complex 57a $^1$H NMR ($CDCl_3$): δ 7.61 (d, 4H); 7.49 (d, 4H); 6.58 (m, 2H); 6.44 (m, 2H); 5.94 (m, 2H); 2.18 (s, 6H).

Complex 58:

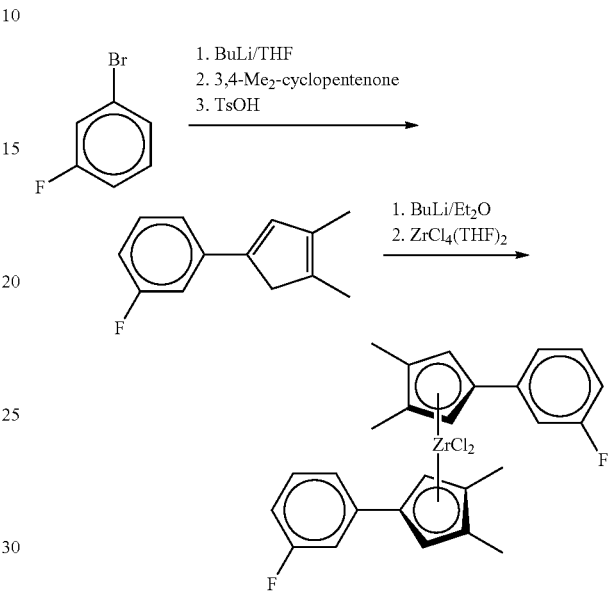

1-(3,4-Dimethyl-1,3-cyclopentadien-1-yl)-3-fluorobenzene

The solution of 1-bromo-3-fluorobenzene (12 g, 70 mol) in 100 mL of $Et_2O$ was cooled to −50° C., and BuLi (44 mL, 1.6 M in hexane, 70 mmol) was added. The mixture was stirred at this temperature for 1 h and warmed to 0° C. The solution of 3,4-dimethylcyclopenen-2-one (7.7 g, 70 mmol) in 10 mL of ether was added, the mixture was stirred overnight, and treated by 30 mL of water. Organic layer was separated, washed by brine and the solvent was removed. Benzene (50 mL) and TsOH (0.5 g) were added, and the mixture was refluxed for 1 min. After cooling the mixture was washed by 5% $NaHCO_3$, brine, dried over $MgSO_4$, filtered through silica gel. Solvent was removed, and the residue was recrystallized from methanol, yielding 6.3 g of product (48%).

$^1$H NMR ($CDCl_3$): δ 7.40 (m, 2H); 6.99 (m, 2H); 6.59 (s, 1H); 3.24 (s, 2H); 1.99 (s, 3H); 1.91 (s, 3H).

The solution of 1-(3,4-dimethyl-1,3-cyclopentadien-1-yl)-3-fluorobenzene (5 g, 26 mmol) in $Et_2O$ (50 mL) was cooled to −30° C., and BuLi (16.5 mL, 1.6 M in hexane, 26 mmol) was added dropwise. The mixture was stirred 2 h at room temperature, cooled to 0° C., and $ZrCl_4(THF)_2$ (4.9 g, 13 mmol) was added. After 16 h of stirring, reaction mixture was filtered, solid residue was washed with ether and the solvent was evaporated. Residue was extracted by 50 mL of benzene-hexane mixture (1:1), and the yellow precipitate was filtered and dried in vacuo. The yield was 4 g (58%).

$^1$H NMR ($CDCl_3$): δ 7.43 (m, 4H); 7.15 (m, 3H); 6.21 (m, 4H); 1.80 (s, 12H).

Complex 59:

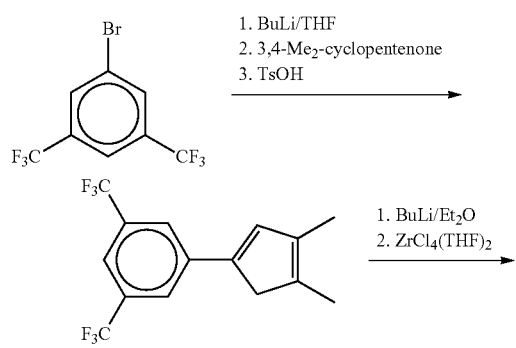

1-(3,4-Dimethyl-1,3-cyclopentadien-1-yl)-3,5-bis(trifluoromethyl)benzene

The solution of 1-bromo-3,5-bis(trifluoromethyl)benzene (10 g, 34 mmol) in 50 mL of $Et_2O$ was cooled to −70° C., and BuLi (22 mL, 1.6 M in hexane, 35 mmol) was added. The mixture was stirred at this temperature for 1 h, 3,4-dimethylcyclopenen-2-one (3.3 g, 30 mmol) in 10 mL of ether was added, the mixture was stirred overnight, and treated by 20 mL of water. Organic layer was separated and washed by brine. TsOH (0.5 g) was added, and the mixture was refluxed for 3 min. After cooling the mixture was washed by 5% $NaHCO_3$, brine, dried over $MgSO_4$, solvent was evaporated and the residue was recrystallized from methanol, yielding 4.7 g (63%) of the product.

$^1$H NMR ($CDCl_3$): δ 7.81 (s, 2H); 3.61 (s, 1H); 6.87 (s, 1H); 3.32 (s, 2H); 2.03 (s, 3H); 1.94 (s, 3H).

The solution of 1-(3,4-dimethyl-1,3-cyclopentadien-1-yl)-3,5-bis(trifluoromethyl)benzene (2.4 g, 8 mmol) in $Et_2O$ (30 mL) was cooled to −30° C., and BuLi (5 mL, 1.6 M in hexane, 8 mmol) was added dropwise. The mixture was stirred 2 h at room temperature, cooled to 0° C., and $ZrCl_4(THF)_2$ (1.5 g, 4 mmol) was added. After 16 h of stirring, the mixture was filtered, filtrate was evaporated. Residue was treated with pentane, yellow precipitate was filtered off and dried in vacuo. The yield was 0.9 g (29%).

$^1$H NMR ($CDCl_3$): δ 7.77 (br s, 6H); 6.25 (s, 4H); 1.86 (s, 12H).

Complex 62

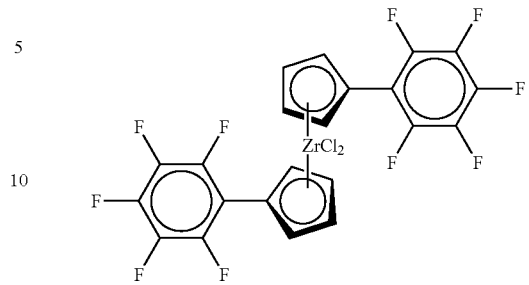

Complex 62 was synthesized as described in *Organometallics*, 1996, 15, 5287.

Complex 60:

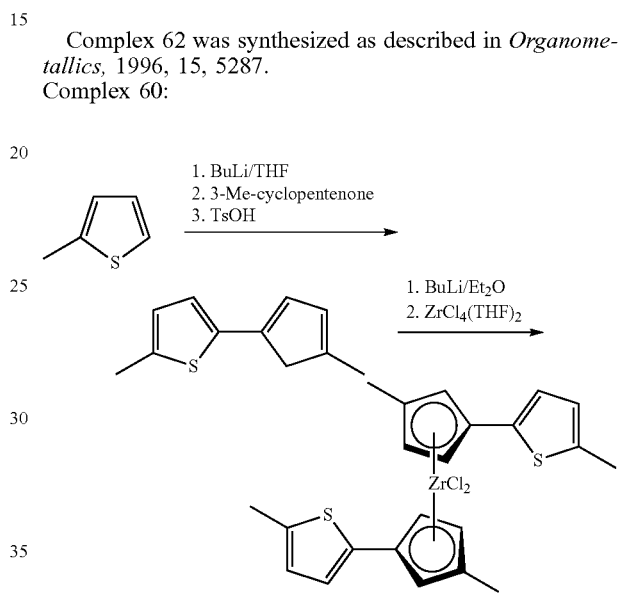

2-Methyl-5-(4-methyl-1,4-cyclopentadien-1-yl)thiophene

The solution of 2-methylthiophene (9.8 g, 100 mmol) in 100 mL of $Et_2O$ was cooled to −30° C., and BuLi (50 mL 2.5N in hexane, 80 mmol) was added. The mixture was stirred at this temperature for 40 min, warmed to 0° C., and 3-methylcyclopenen-2-one (7.7 g, 80 mmol) in 10 mL of ether was added. After 16 h of stirring, the mixture was treated by 30 mL of water, organic layer was separated, washed by brine and concentrated to 100 mL. TsOH (0.5 g) was added, and the mixture was refluxed for 1 min. After cooling the mixture was washed by 5% $NaHCO_3$, brine, dried over $MgSO_4$, solvent was evaporated and the residue was distilled in vacuo, yielding 5.5 g of product as a mixture of 3 isomers (39%, b.p. 90-94° C./1 torr).

$^1$H NMR ($CDCl_3$): δ 6.83 (gr. signals, 1H); 6.64 (m, 1H); 6.45 (gr. signals, 1H); 6.07 (gr. signals, 1H); 3.21 (gr. signals, 2H); 2.49 (gr. signals, 3H); 2.08 (gr. signals, 3H).

The solution of 2-(3,4-dimethyl-1,3-cyclopentadien-1-yl)-5-methylthiophene (3.52 g, 20 mmol) in $Et_2O$ (30 mL) was cooled to −20° C., and BuLi (8 mL 2.5N in hexane, 20 mmol) was added dropwise. Suspension obtained was stirred 2 h at room temperature, cooled again to −20° C., and $ZrCl_4(THF)_2$ (3.77 g, 10 mmol) was added. After 16 h of stirring the precipitate was filtered, dissolved in dichloromethane, solution was filtered and solvent was evaporated. The residue was washed with pentane and dried in vacuo giving 1.6 g (31%) of the product as a mixture of isomers (1:2 ratio).

¹H NMR (CDCl₃): δ 6.92 (m, 2H); 6.70 (m, 2H); 6.36 (m, 2H); 6.33 (m, 2H); 5.76 (m, 2H); 2.53 (2 s, 6H); 2.14 and 2.09 (2 s, 6H).

Complex 66:

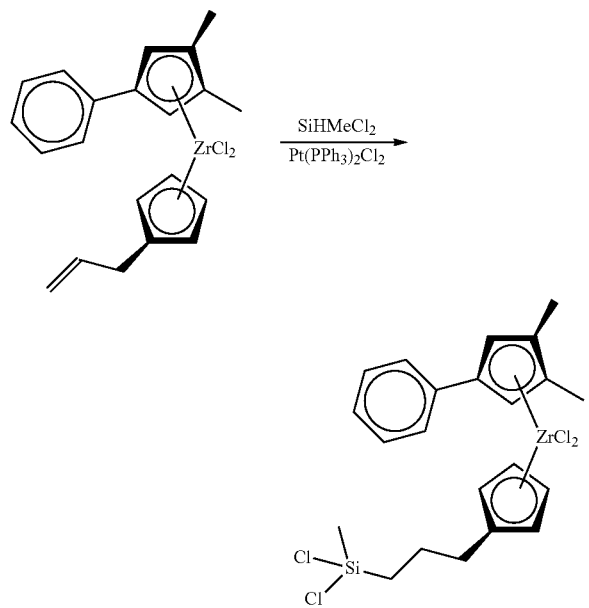

Pt(PPh₃)₂Cl₂ (35 mg, 44 mmol) was added to solution of complex 342 (0.96 g, 2.2 mmol) and SiHMeCl₂ (0.51 g, 4.4 mmol) in toluene (20 mL). The mixture was heated with stirring at 60° C. for 6 h, and 16 h at room temperature. The solvent was removed under reduced pressure, and the residue was recrystallized from pentane yielding 0.56 g (59%) of the product.

¹H NMR (CDCl₃): δ 7.51 (d, 2H); 7.44 (t, 2H); 7.30 (t, 1H); 6.61 (s, 2H); 5.95 (bs, 2H); 5.90 (bs, 2H); 2.54 (t, 4H); 1.63 (m, 4H); 1.04 (m, 4H); 0.74 (s, 6H).

¹³C NMR (CDCl₃): δ 133.87; 133.49; 129.15; 128.40; 127.59; 125.13; 121.90; 117.21; 114.10; 114.07; 32.42; 23.57; 21.24; 13.84; 5.13.

Example 2

Polymerization Methodology

All metal complexes were tested for ethylene-butene co-polymerization in identical, commercially relevant slurry polymerization conditions in a standard MAO-activated (Al/M=100) and silica-supported catalyst recipe, prepared using the pore filling (incipient wetness) method described below.

Preparation of supported catalysts: According to a general recipe, 5.05×10⁻⁵ moles of complex were dissolved in 1.2 mL of 30% MAO, corresponding to Al/metal ratio of 100. After 30 minutes stirring at ambient temperature, the resulting solution was slowly and evenly added drop wise to a stirred bed of Davison 948 silica, calcined for 6 h at 600° C. After 15 minutes of further stirring, the catalyst was vacuum-dried for 15 minutes. The catalysts were usually tested within 24 hours of preparation.

Catalyst Testing: To a dry 2 L stainless steel autoclave charged with 1 L of iso-butane, 100 ml, of 1-butene and 2 mL of 1M TIBAL solution and saturated at 70° C. with 15.5 bar (225 psi) partial pressure with ethylene, a catalyst charge (0.05 g to 0.1 g) was injected in iso-butane to start the polymerization. The ethylene was supplied on demand in order to maintain the reactor pressure. In runs with H₂, the hydrogen gas was dosed in before the run from a 7 mL or a 300 mL H₂ vessel pressurized to the initial pressure of 600 psi and quantified by a specific pressure drop (e.g., 20 Δ psi). After 1 hour, the polymerization was terminated by venting the reactor. The dried polymer samples were analyzed by GPC, FT-IR and rheological tests.

Example 3

Catalytic Activity of Trifluoromethyl Substituted Zirconocenes and Heteroaryl Substituted Zirconocenes

TABLE 2

Performance of the Metallocene Catalysts

| Run # | A, g/g/h | A, kg/mol/h | Mw | Mw/Mn | Br/1000 | Eta100 | Er |
|---|---|---|---|---|---|---|---|
| 1 | 1,195 | 48,235 | 197,000 | 2.4 | 23 | 57,400 | 0.74 |
| 2 | 1,478 | 55,992 | 197,755 | 2.84 | 24.4 | 50,200 | 1.9 |
| 3 | 433 | 32,994 | 329,407 | 3.32 | 27.6 | 76,600 | 0.95 |
| 4 | 423 | 14,887 | 316,662 | 3.2 | 26.2 | 62,900 | 0.76 |
| 5 | 482 | 16,641 | 279,000 | 3.2 |  | 56,100 | 0.83 |
| 6 | 1,640 | 71,820 | 101,283 | 2.83 | 25 | 16,100 | 0.27 |
| 7 | 437 | 20,570 | 149,315 | 3.71 | 17.8 | 26,400 | nr |
| 8 | 49 | 1,871 | 54,200 | 4.43 | 24 | 3,000 | 1.77 |
| 9 | 1,325 | 45,263 | 234,000 | 2.71 | 17.3 | 66,800 | 0.83 |
| 10 | 3,145 | 115,697 | 116,359 | 2.34 | 22.7 | 22,100 | 0.35 |
| 11 | 1,439 | 49,708 | 116,000 | 2.49 | 18.9 | 20,700 | nr |
| 12 | 1,976 | 77,169 | 107,000 | 2.4 | 27.4 | 18,700 | 0.27 |
| 13 | 2,139 | 86,030 | 107,615 | 2.26 | 26.6 | 17,600 | 0.19 |
| 14 | 2,315 | 64,356 | 128,000 | 2.53 | 21 | 25,000 | 0.44 |
| 15 | 881 | 41,601 | 91,400 | 3.09 | 19 | 10,600 | nr |
| 16 | 50 | 1,857 | 185,011 | 5.9 |  |  |  |

TABLE 2-continued

Performance of the Metallocene Catalysts

| Run # | A, g/g/h | A, kg/mol/h | Mw | Mw/Mn | Br/1000 | Eta100 | Er |
|---|---|---|---|---|---|---|---|
| 17 | 399 | 12,475 | 384,000 | 3.11 | 25.1 | 81,900 | 0.54 |
| 18 | 174 | 6,370 | 382,000 | 3.56 | 26.7 | 75,500 | 0.77 |
| 19 | 1,749 | 84,340 | 172,316 | 2.83 | 18.3 | 36,100 | 2.24 |
| 20 | 279 | 10,621 | 168,490 | 5.09 | 27.2 | 23,500 | 1 |
| 21 | 2,110 | 75,756 | 145,550 | 2.7 | 18.4 | 32,800 | 0.46 |
| 22 | 106 | 7,015 | 223,954 | 5.58 | 17 | 29,300 | 5.13 |
| 23 | 2,347 | 74,973 | 118,000 | 2.66 | 20.3 | 20,600 | 0.27 |
| 24 | 2,669 | 120,860 | 128,000 | 2.49 | 18.6 | 23,400 | nr |
| 25 | 575 | 19,609 | 167,871 | 3.66 | 15.4 | 36,900 | 0.58 |
| 26 | 0 | 0 | | n/a | n/a | | n/a |
| 27 | 604 | 18,219 | 142,929 | 2.93 | 14.9 | 29,500 | 0.67 |
| 28 | 1,021 | 33,284 | 118,207 | 3.64 | 10 | 16,700 | 0.42 |
| 29 | 267 | | 182,000 | 8.9 | 18.4 | 27,600 | 2.61 |
| 30 | 1,200 | 57,448 | 235,265 | 3.5 | 19.2 | 41,100 | 2.25 |
| 31 | 232 | 8,914 | 336,000 | 6.25 | 19.9 | 72,500 | 0.52 |
| 32 | 0 | 0 | | n/a | n/a | | n/a |
| 33 | 450 | 16,452 | 164,407 | 2.04 | 8.2 | 29,500 | nr |
| 34 | 21 | 611 | 181,380 | 2.97 | | | n/a |
| 35 | 64 | 4,579 | 263,427 | 4.29 | 15.9 | 25,900 | 6.95 |
| 36 | 56 | 4,398 | 289,502 | 5.14 | 17.9 | 37,300 | 6.63 |
| 37 | 1,073 | 35,342 | 148,000 | 3.47 | 20.1 | 31,100 | 0.59 |
| 38 | 876 | 34,689 | 157,000 | 3.65 | 18.3 | 31,500 | 0.54 |
| 39 | 1,095 | 33,719 | 455,734 | 2.76 | 26.4 | 94,800 | |
| 40 | 336 | 13,615 | 511,856 | 2.5 | 28.3 | 95,000 | nr |
| 41 | 1,118 | 42,452 | 526,720 | 3.12 | 17.8 | 92,000 | nr |
| 42 | 61 | 2,340 | 505,557 | 3.13 | 2.6 | 86,000 | nr |
| 43 | 526 | 21,417 | 318,420 | 2.79 | 18 | 71,700 | nr |
| 44 | 938 | 41,005 | not sol. | | 19.1 | 80,300 | nr |
| 45 | 1,012 | 30,206 | 354,000 | 3.15 | 19.3 | 84,400 | nr |
| 46 | 689 | 27,821 | 549,000 | 4.13 | 14.3 | 101,000 | nr |
| 47 | 79 | 3,790 | 117,000 | 3.93 | 8 | | |
| 48 | 1,227 | 34,594 | not sol. | | 17.3 | 78,200 | nr |
| 49 | 445 | 15,654 | 357,700 | 3.4 | 14.6 | 71,900 | nr |
| 50 | 1,591 | 65,481 | 396,341 | 2.74 | 12.4 | 71,200 | |
| 51 | 487 | 13,899 | 532,000 | 5.87 | 22.3 | 96,100 | nr |
| 52 | 2,182 | 64,861 | 340,000 | 2.83 | 23.6 | 66,200 | 22.4 |
| 53 | 2,100 | 60,589 | 294,000 | 2.47 | 14.8 | no melt | |
| 54 | 1,647 | 52,076 | 545,000 | 3.82 | 18.1 | 96,000 | nr |
| 55 | 864 | 29,136 | 469,000 | 2.62 | 16 | 101,000 | nr |
| 56 | 1,623 | 59,713 | 426,000 | 2.59 | 20 | 76,000 | |
| 57 | 991 | 36,576 | 359,000 | 2.73 | 18.5 | 79,600 | |
| 58 | 250 | 6,441 | 419,000 | 2.97 | | 91,400 | |
| 59 | 882 | 31,673 | 743,000 | 2.94 | 18.9 | 95,800 | nr |
| 60 | 1,680 | 51,084 | 310,000 | 2.8 | 17.1 | 75,400 | 33.8 |
| 61 | 366 | 11,214 | 366,000 | 2.57 | 17.2 | 84,100 | 51.3 |
| 62 | 0 | 0 | | | | | |
| 63 | 158 | 5,160 | 202,801 | 3.24 | 16 | 46,100 | 3.46 |
| 64 | 1,926 | 55,265 | 158,000 | 2.5 | 20 | 35,000 | 0.64 |
| 65 | 1,789 | 64,438 | 167,000 | 2.55 | 17.7 | 42,500 | 1.32 |
| 66 | 2,408 | 77,486 | 192,000 | 2.48 | 16 | 49,600 | 2.31 |
| 67 | 2,003 | 75,596 | 181,000 | 2.56 | 12.3 | 45,000 | 0.66 |
| 68 | 1,149 | 43,022 | 197,000 | 2.74 | 14.8 | 52,200 | 2.93 |
| 69 | 57 | 2,066 | 169,000 | 3.75 | 11.8 | | |
| 70 | 1,925 | 77,672 | 149,015 | 2.62 | 21.9 | 36,300 | 1.54 |

Table 2 highlights the performance of various different metallocene catalysts (R#42, R#50, R#52-57, and R#59-60) and a set of reference compounds (R#1-5). In particular the table highlights the enhanced performance of the catalysts over the reference catalysts with increased molecular weight, activity or decreased branching of the polymer chain.

Example 4

Use of Cocatalysts with Zirconocenes to Control Polymer Microstructure

TABLE 3

Varying Amounts of Al/Zr Changes Polymer Properties

| Al/Zr | A, g/g | A, kg/molZr/h | Mw | Mw/Mn |
|---|---|---|---|---|
| 61 | 3,504 | 75,846 | 176,000 | 18.2 |
| 101 | 2,825 | 83,979 | 141,000 | 9.6 |
| 152 | 1,385 | 74,939 | 35,800 | 5.0 |

* * *

All of the compounds, complexes, and methods disclosed and claimed herein can be made and executed without undue experimentation in light of the present disclosure. While the compounds, complexes, and methods of this invention have been described in terms of preferred embodiments, it will be apparent to those of skill in the art that variations may be applied to the compounds, complexes, and methods, as well as in the steps or in the sequence of steps of the method described herein without departing from the concept, spirit, and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 4,752,597
U.S. Pat. No. 6,756,455
U.S. Pat. No. 7,723,450
U.S. Pat. No. 8,435,911
WO 1997/036937
WO 1999/006414
WO 2000/031090
WO 2005/103096
Anderson, N. G., *Practical Process Research & Development—A Guide For Organic Chemists*, 2$^{nd}$ ed., Academic Press, New York, 2012.
Cotton and Wilkinson, "Advanced Inorganic Chemistry," 5$^{th}$ Ed., John Wiley & Sons, New York, 1988
Deck, et al., "Synthesis of Pentafluorophenyl-Substituted Cyclopentadienes and Their Use as Transition-Metal Ligands," *Organometallics*, 15(25):5287-5291, 1996.
*Handbook of Polymer Synthesis: Second Edition*, Eds.: Hans R. Kricheldorf, Oskar Nuyken, and Graham Swift., CRC Press, 2004.
*March's Advanced Organic Chemistry: Reactions, Mechanisms, and Structure*, 2007.
Odian, *Principles of Polymerization*, 4$^{th}$ Edition, Wiley-Interscience, 2004.

What is claimed is:

1. A composition for the production of a polymer comprising an activating compound and a compound of the formula:

$$\begin{array}{c} L_1 \diagdown \quad \diagup Y_1 \\ M \\ L_2 \diagup \quad \diagdown Y_2 \end{array} \quad (I)$$

wherein:
$L_1$ and $L_2$ are each independently selected from the group consisting of:

M is a transition metal of Group 4; and
$Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, aralkyloxylate, or a substituted version of any of these groups;

where if $X_1$ is alkyl$_{(C\leq 3)}$, then $X_2$, $X_3$, and $X_4$ are not all hydrogen or alkyl$_{(C\leq 8)}$; and wherein M is Ti, Zr, or Hf; and wherein the polymer contains less than 10% long chain branching.

2. The composition of claim 1, wherein $Y_1$ and $Y_2$ are each independently chloride.

3. The composition of claim 1, further defined as:

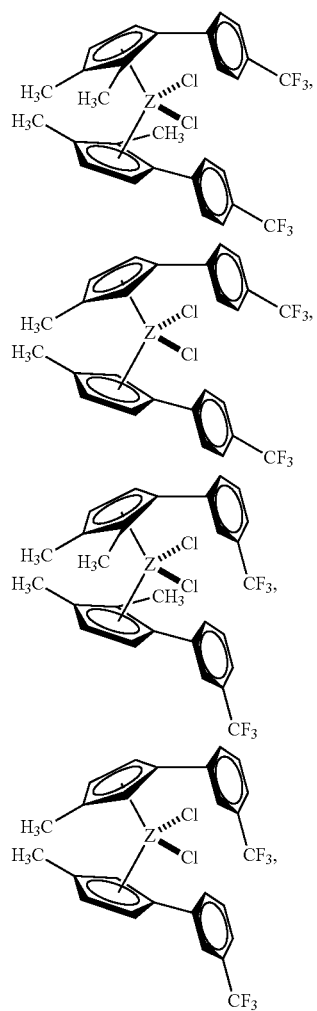

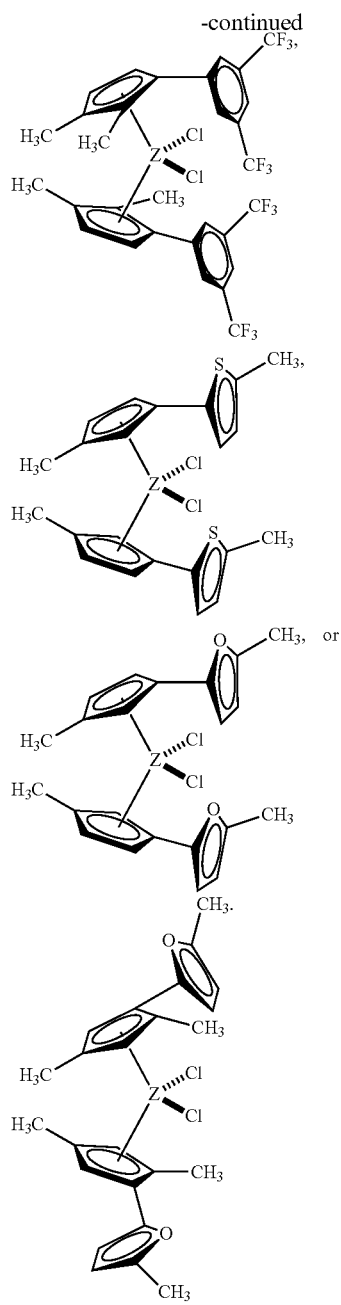

4. The composition of claim 1, wherein the activating compound is aluminoxane.

* * * * *